(12) United States Patent
Malewicz et al.

(10) Patent No.: US 10,695,089 B2
(45) Date of Patent: Jun. 30, 2020

(54) MEDICAL TOOLS AND METHODS FOR GAINING ACCESS TO EXTRAVASCULAR SPACES

(71) Applicant: Medtronic, Inc., Minneapolis, MN (US)

(72) Inventors: Andrzej M. Malewicz, Minneapolis, MN (US); Ronald A. Drake, St. Louis Park, MN (US); Keith D. Anderson, Minneapolis, MN (US); Roger A. Christopherson, Vadnais Heights, MN (US); Andrea J. Asleson, Maple Grove, MN (US); Trent M. Fischer, St. Paul, MN (US); Lester O. Stener, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 578 days.

(21) Appl. No.: 15/204,579

(22) Filed: Jul. 7, 2016

(65) Prior Publication Data
US 2017/0007287 A1   Jan. 12, 2017

Related U.S. Application Data

(60) Provisional application No. 62/190,885, filed on Jul. 10, 2015, provisional application No. 62/236,201, filed on Oct. 2, 2015.

(51) Int. Cl.
*A61B 17/34* (2006.01)
*A61N 1/05* (2006.01)
(Continued)

(52) U.S. Cl.
CPC ......... *A61B 17/3468* (2013.01); *A61B 17/32* (2013.01); *A61B 17/3415* (2013.01);
(Continued)

(58) Field of Classification Search
CPC ....... A61B 2017/320044; A61B 2017/320056; A61B 17/3415; A61B 2090/0811; A61B 17/3468; A61N 1/0563
See application file for complete search history.

(56) References Cited

U.S. PATENT DOCUMENTS 4,687,471 A   8/1987  Twardowski et al.
6,596,001 B2 * 7/2003  Stormby .......... A61B 17/06109
                                                    600/29

(Continued)

OTHER PUBLICATIONS

Medtronic, Inc. 6996T Tunneling Tool, Technical Manual, 12 pages.
(Continued)

*Primary Examiner* — Sarah W Aleman

(57) ABSTRACT

This disclosure provides tools and implant techniques utilizing such tools to gain access to and implant a medical device, such as a medical electrical lead, within extravascular spaces. In one example, this disclosure provides a tool for creating a sub-sternal tunnel in a patient. The tool comprises a relatively straight guide member extending from a first end thereof to a second end thereof, a tunneling member extending from a first end thereof to a tip thereof, the tunneling member extending alongside and coplanar with the guide member, the first end of the tunneling member and the first end of the guide member being joined together, and a handle coupled to the guide member.

25 Claims, 23 Drawing Sheets

(51) Int. Cl.
 *A61B 17/32* (2006.01)
 *A61N 1/372* (2006.01)
 *A61B 17/00* (2006.01)
 *A61B 90/00* (2016.01)

(52) U.S. Cl.
 CPC .. *A61N 1/0563* (2013.01); *A61B 2017/00243* (2013.01); *A61B 2017/00424* (2013.01); *A61B 2017/320044* (2013.01); *A61B 2017/320052* (2013.01); *A61B 2017/320056* (2013.01); *A61B 2090/0811* (2016.02); *A61N 1/05* (2013.01); *A61N 1/0504* (2013.01); *A61N 1/372* (2013.01)

(56) References Cited

U.S. PATENT DOCUMENTS

| | | |
|---|---|---|
| 8,574,192 B2 | 11/2013 | Haarala et al. |
| 2006/0015130 A1 | 1/2006 | Voorhees, Jr. et al. |
| 2009/0088599 A1* | 4/2009 | Zook ................ A61B 17/3403 600/29 |
| 2012/0083794 A1 | 4/2012 | Martin et al. |
| 2014/0330208 A1 | 11/2014 | Christie et al. |
| 2015/0133951 A1 | 5/2015 | Seifert et al. |
| 2015/0133953 A1 | 5/2015 | Seifert et al. |
| 2015/0202408 A1* | 7/2015 | McMurtry ......... A61B 17/0401 604/510 |
| 2015/0306375 A1 | 10/2015 | Marshall et al. |
| 2015/0306410 A1 | 10/2015 | Marshall et al. |
| 2016/0158567 A1 | 6/2016 | Marshall et al. |

OTHER PUBLICATIONS

Spine Surgical Innovation Catalog, 2011; 52 pages.
(PCT/US2016/0141423) PCT Notification of Transmittal of the International Search Report and the Written Opinion of the International Searching Authority, dated Oct. 27, 2016, 11 pages.

* cited by examiner

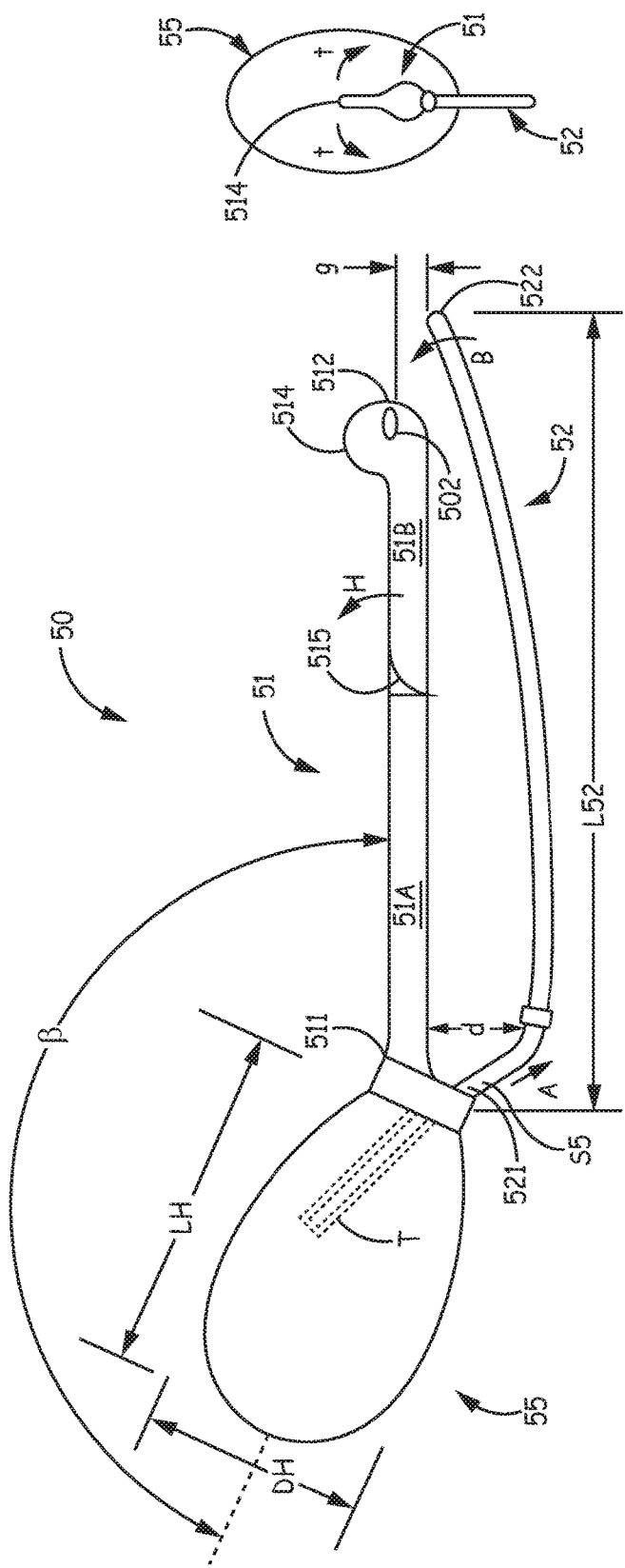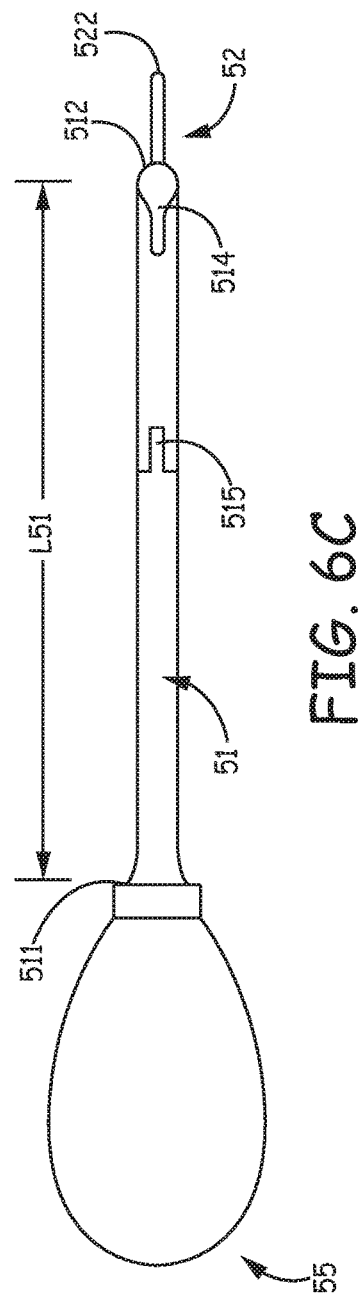
FIG. 6A
FIG. 6B
FIG. 6C

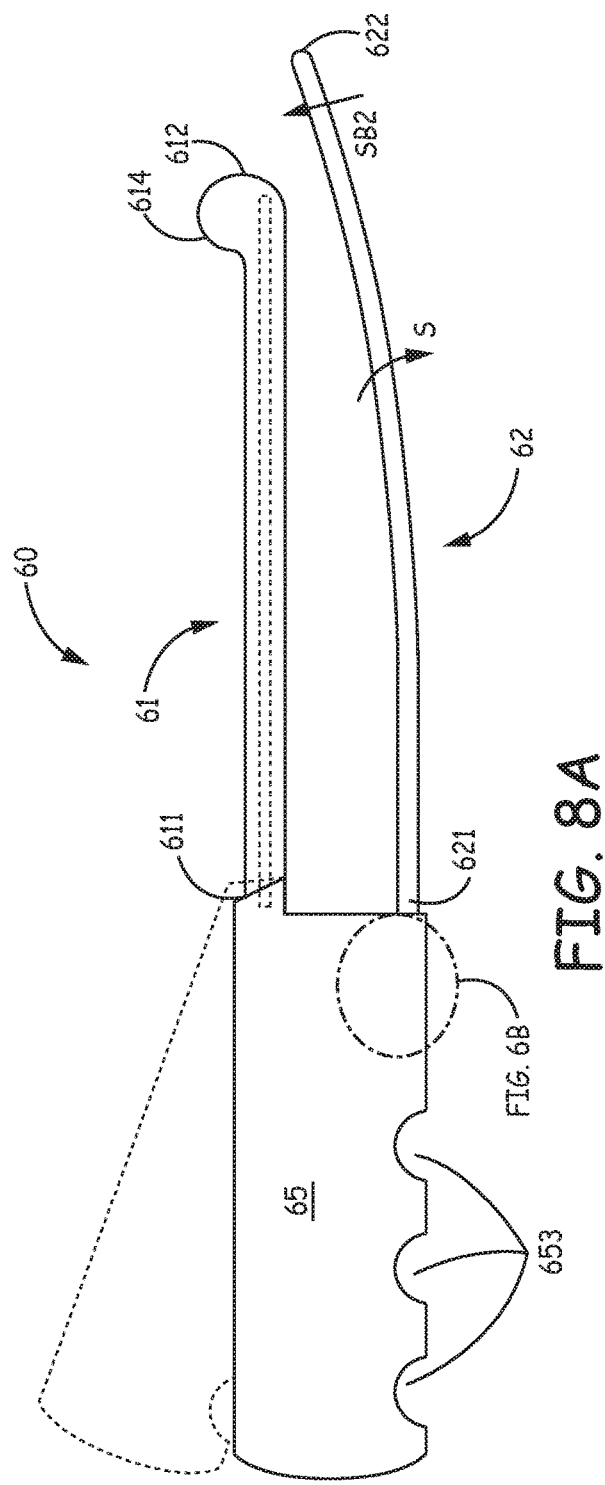
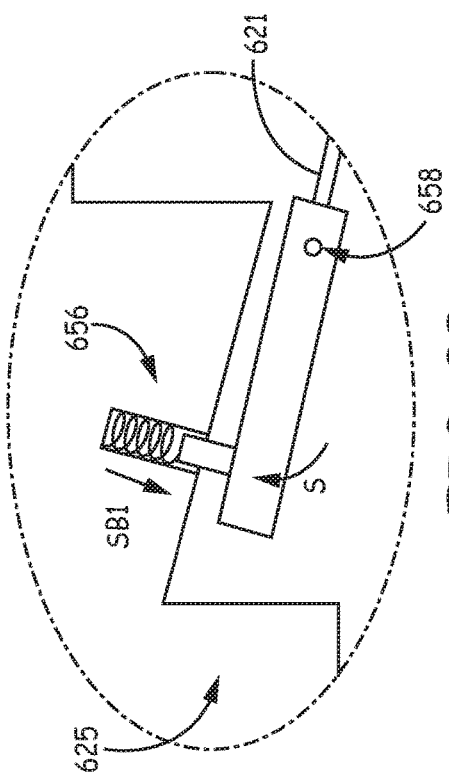

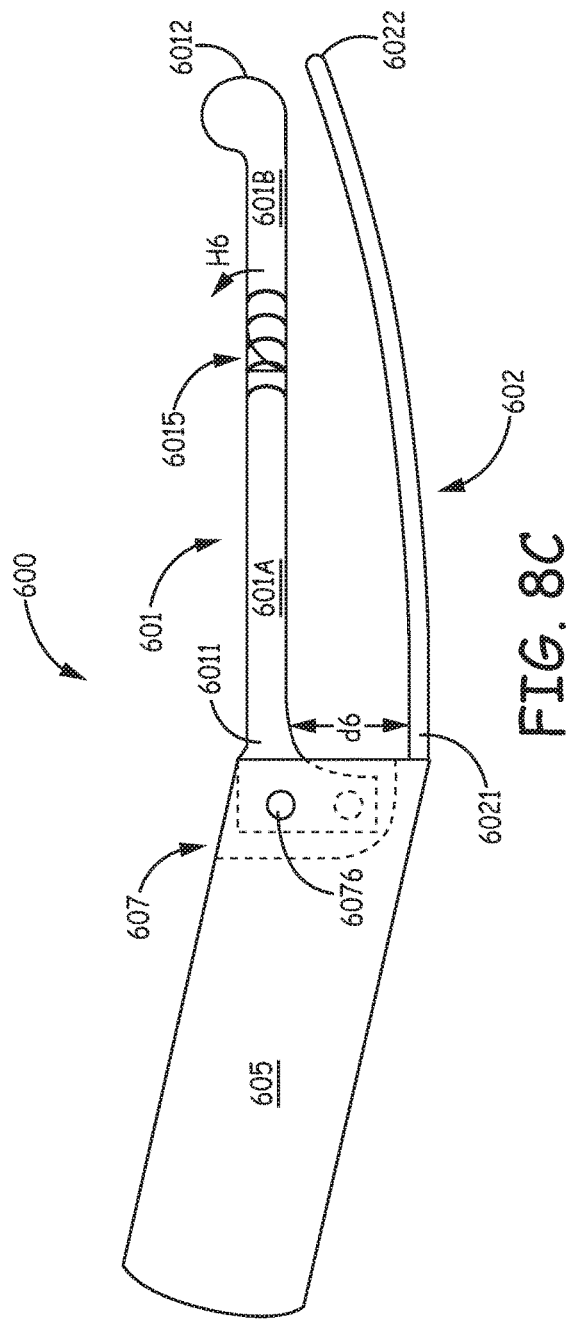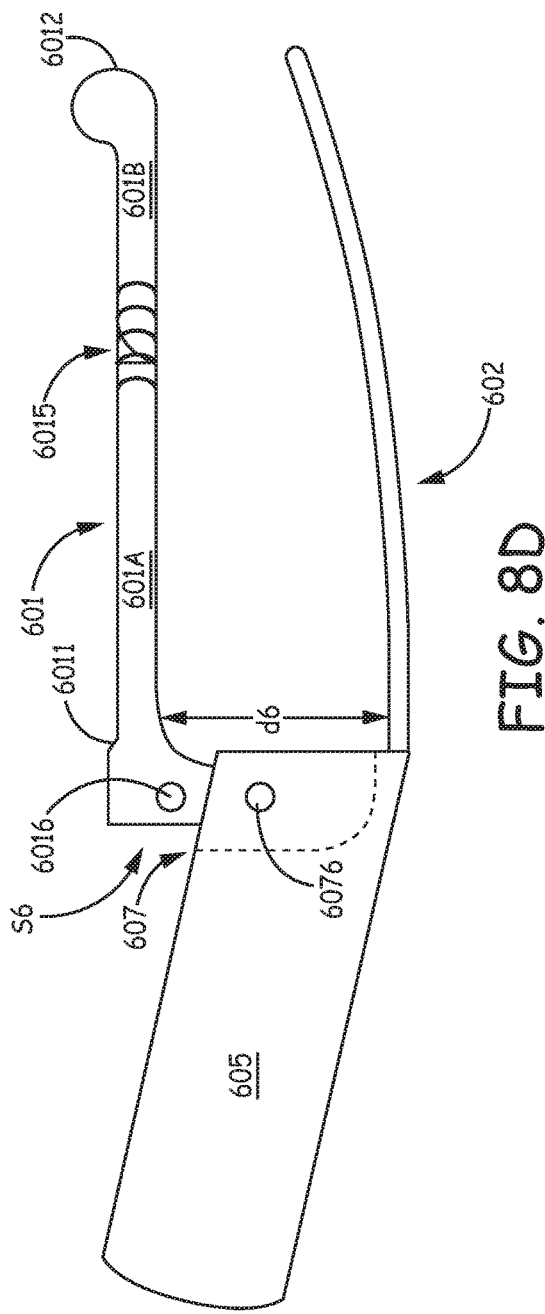

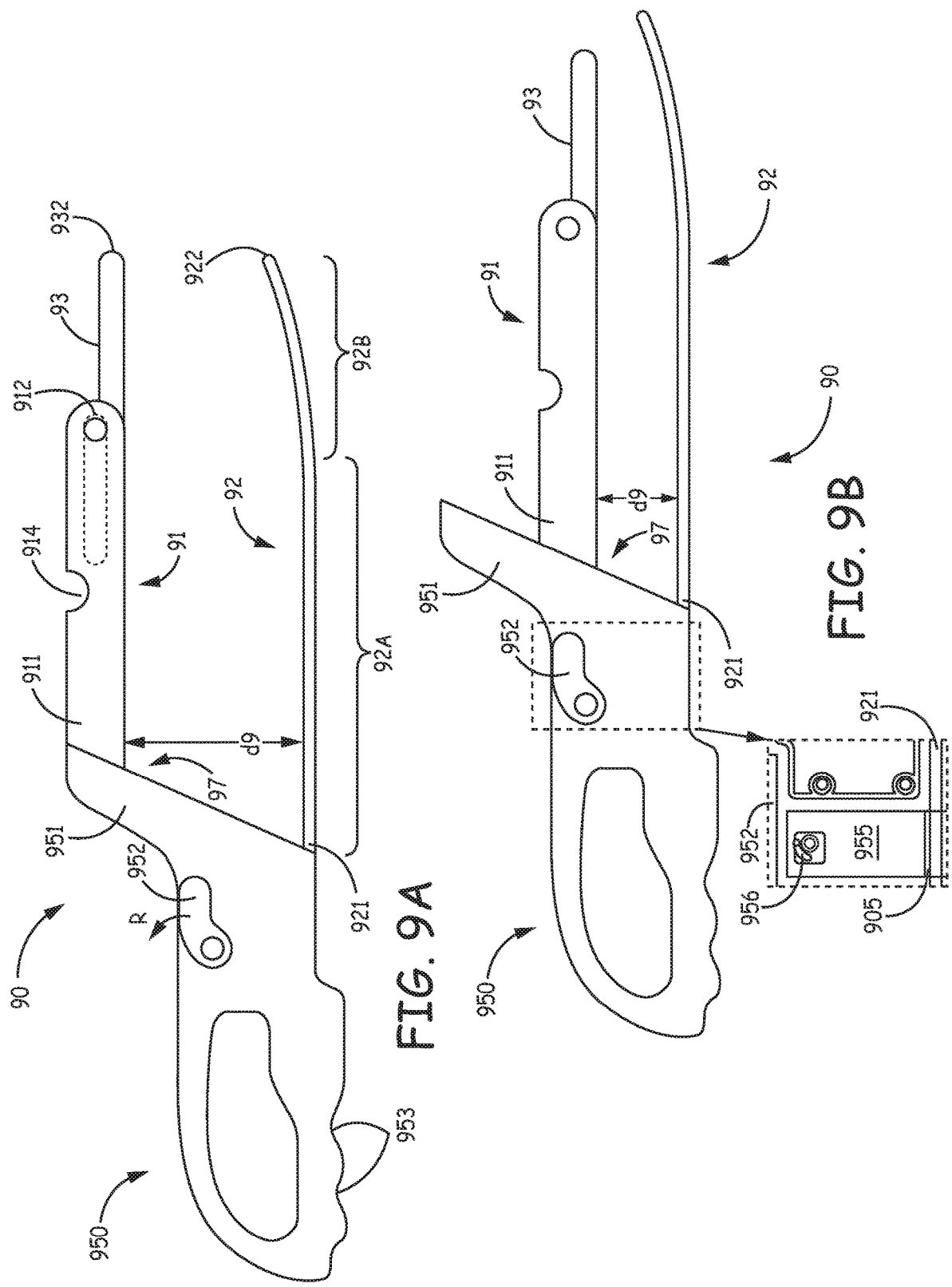

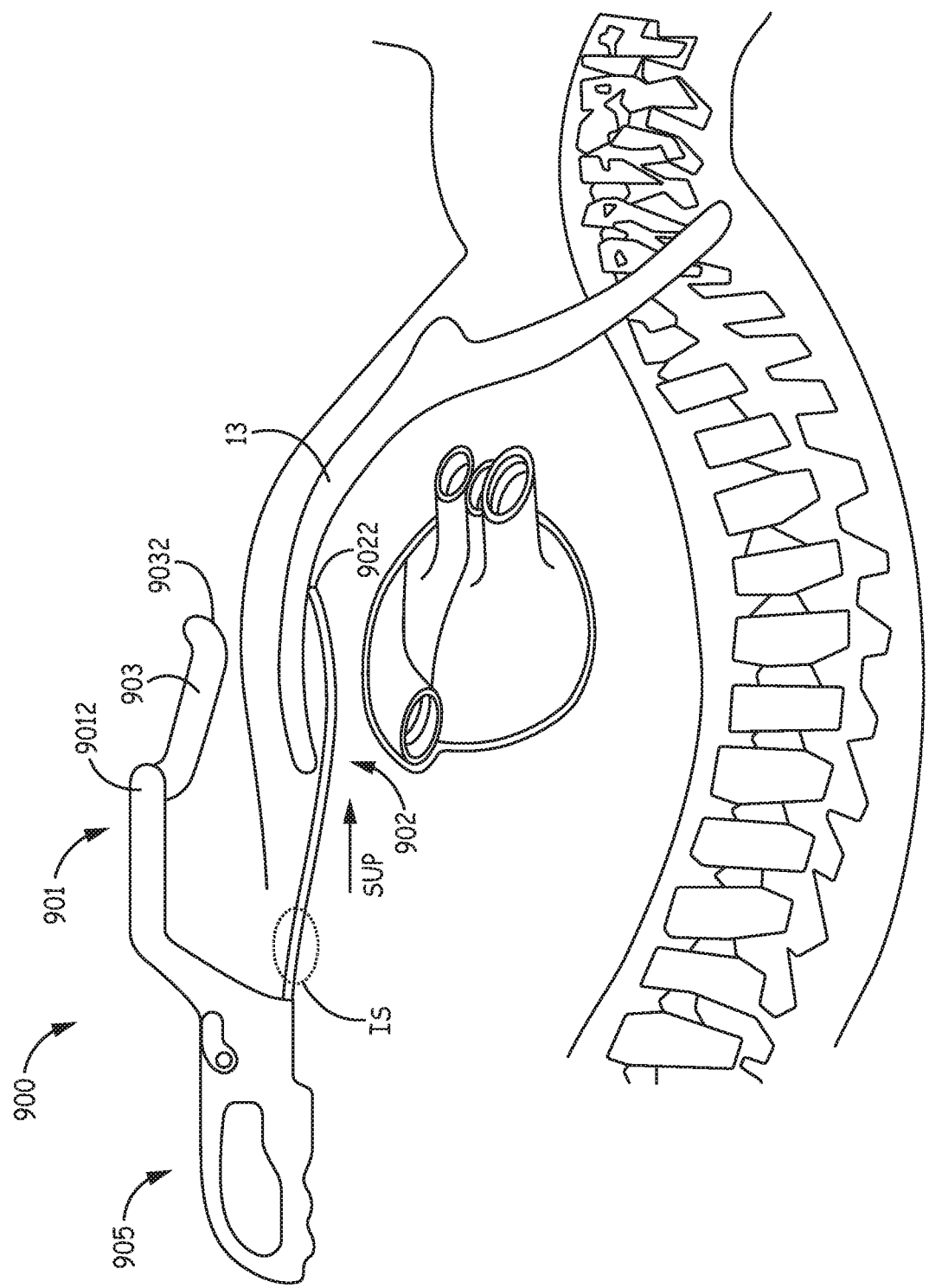

MEDICAL TOOLS AND METHODS FOR GAINING ACCESS TO EXTRAVASCULAR SPACES

TECHNICAL FIELD

The present disclosure pertains to tools and associated methods for safely gaining access to extravascular spaces, and more particularly to those suited to safely gain access into a sub-sternal space for the positioning of a medical device therein.

BACKGROUND

Implantable medical electrical leads, included in systems that are known in the art for delivering cardiac therapy and/or for providing cardiac monitoring, are often implanted transvenously within a heart of a patient. But extravascular implant sites may be preferred, for example, in those patients where vascular access is difficult, or because transvenous leads can become fibrosed in the heart over time, which makes lead revision and extraction procedures challenging.

SUMMARY

This disclosure provides tools and implant techniques utilizing such tools to gain access and implant a lead within extravascular spaces. In one example, this disclosure provides a tool for creating a sub-sternal tunnel in a patient. The tool comprises a relatively straight guide member extending from a first end thereof to a second end thereof, a tunneling member extending from a first end thereof to a tip thereof, the tunneling member extending alongside and coplanar with the guide member, the first end of the tunneling member and the first end of the guide member being joined together, and a handle coupled to the guide member.

In another example, handle for a tunneling tool comprises a guide member extending from a first end to a second end, an attachment feature configured to reversibly secure the handle to a first end of a tunneling member so that the secured tunneling member extends alongside and coplanar with the guide member, and a gripping portion located in proximity to the attachment feature and the first end of the guide member.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

The following drawings are illustrative of particular exemplary embodiments and do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIGS. 6A-C are a plan view, a corresponding end view, and a top view of another type of tool, according to some additional embodiments.

FIG. 8A is a plan view of yet another type of tool, according to some embodiments.

FIG. 8B is an enlarged detail of a portion of the tool of FIG. 8A.

FIGS. 8C-D are plan views of a variation of the tool shown in FIGS. 8A-B.

FIGS. 9A-B are plan views of a tool, according to some additional embodiments.

FIG. 10C is a schematic depicting the tool of FIGS. 10A-B, according to some embodiments and methods, advanced superiorly beneath a sternum of the patient.

DETAILED DESCRIPTION

The following detailed description is exemplary in nature and is not intended to limit, in any way, the scope, applicability, or configuration of the tools and techniques described in this disclosure. Rather, the following description provides practical examples, and those skilled in the art will recognize that some of the examples may have suitable alternatives.

Figure 1A:
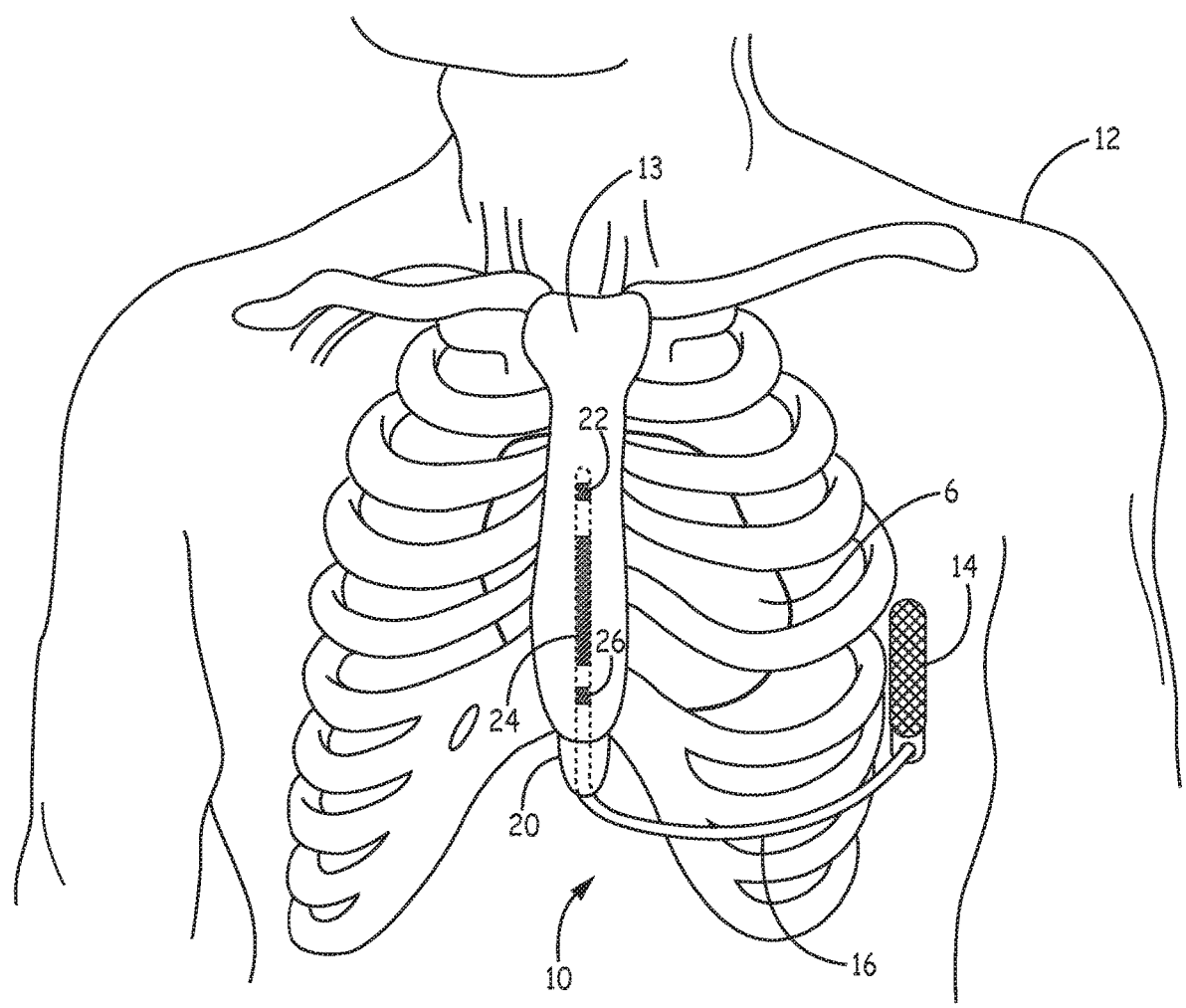
FIGS. 1A-B are schematics showing an exemplary extravascular implant.
Figure 1B:
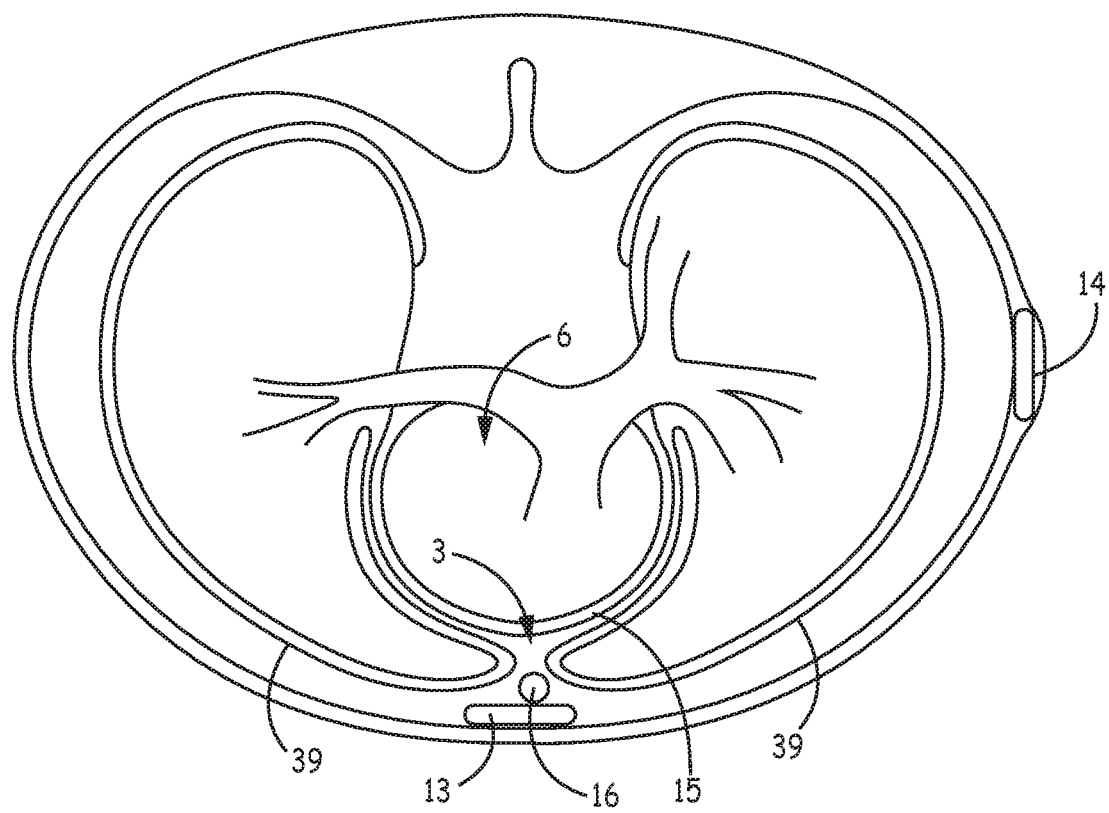

FIGS. 1A-B are schematics showing an exemplary extravascular implant of an exemplary system 10 that includes a pulse generator 14 and an implantable medical electrical lead 16 coupled thereto. Pulse generator 14 is shown implanted subcutaneously on the left mid-axillary of a patient 12, superficially of the patient's ribcage. Pulse generator 14, which may be configured to provide cardiac pacing and/or defibrillation therapy, includes a hermetically sealed housing in which the appropriate electronics and a power supply are contained, and which is formed from a conductive material, such as titanium, or from a combination of conductive and non-conductive materials. Pulse generator 14 further includes a connector module by which lead 16 is electrically coupled to the electronics contained therein, for example, by electrical contacts contained within the connector module and a corresponding hermetically sealed feedthrough assembly, such as is known in the art. The conductive material of device housing may be employed as an electrode, for example, to provide the aforementioned therapy in conjunction with one or more pace/sense electrodes 22, 26 and/or a defibrillation electrode 24 of lead 16, which is shown implanted in a sub-sternal space 3, for example, within the loose connective tissue and/or sub-sternal musculature of the anterior mediastinum. Lead 16 may have any of a number of configurations. For example, lead 16 may include more or fewer pace/sense electrodes. In another example, lead 16 may include more than one defibrillation electrode 24 and/or have a defibrillation electrode that is formed of multiple segments. Examples of leads with multiple defibrillation electrodes and/or segments are described in commonly assigned, co-pending U.S. Patent Publication No. 2015/0306375 (Marshall et al.), U.S. Patent Publication No. 2015/0306410 (Marshall et al.) and U.S. Patent Publication No. 2016/0158567 (Marshall et al.), each of which is incorporated herein by reference in its entirety. With reference to FIG. 1B, the sub-sternal space 3 may be viewed as being bounded laterally by pleurae 39 that enclose the patient's lungs, posteriorly by the pericardial sac 15 that encloses the patient's heart 6, and anteriorly by the sternum 13. In some instances, the anterior wall of the anterior mediastinum may also be formed by the transversus thoracis and one or more costal cartilages. Although FIGS. 1A and 1B are described in the context of the distal portion of lead 16 being placed within the sub-sternal space 3, in other embodiments, the tools and implant techniques described herein may be used to implant a distal portion of the lead 16 at other locations outside the heart. In one example, the tools may be used to place the distal portion of lead 16 intra-pericardially via a percutaneous subxiphoid approach.

Figure 2:
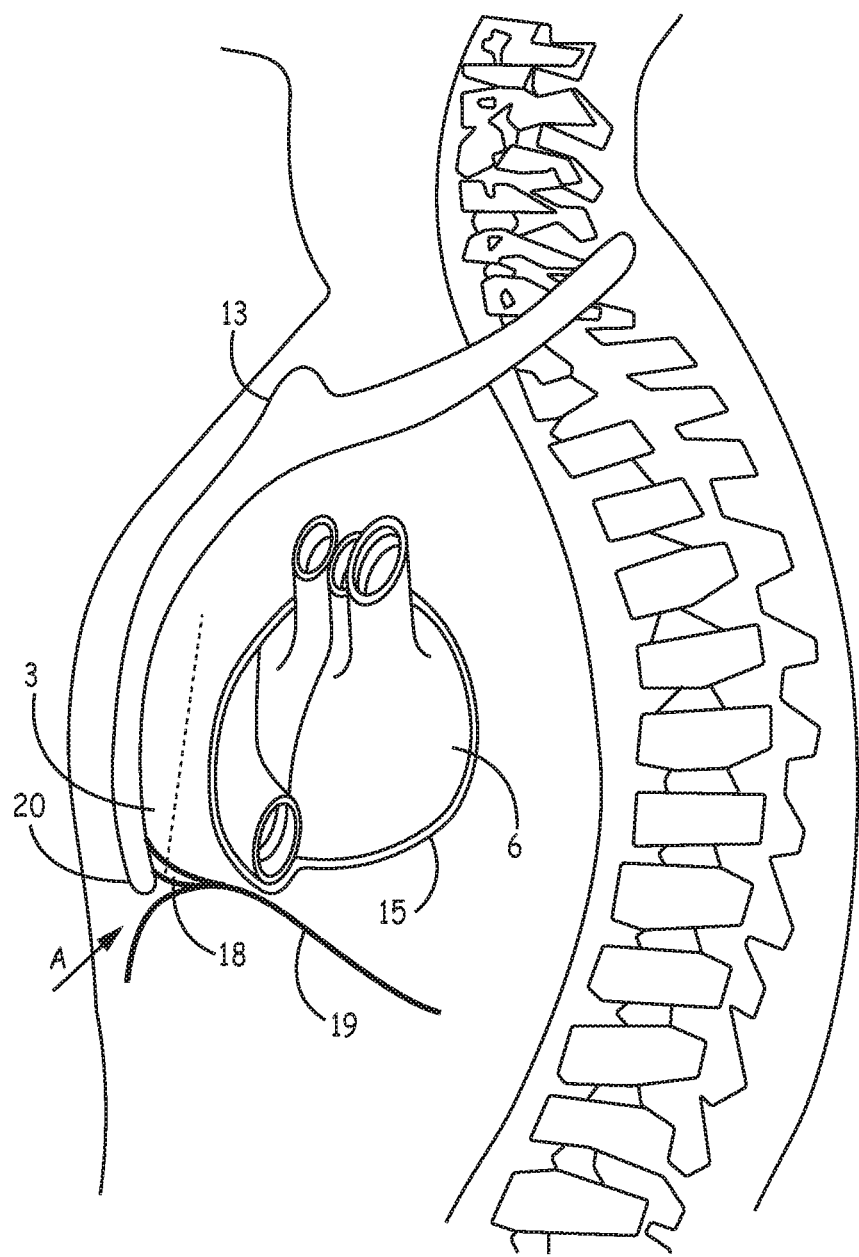
FIG. 2 is a schematic for describing sub-sternal access.

FIG. 2 is a schematic showing an access site A for making a passageway between a patient's diaphragm 19 and xiphoid process 20 of sternum 13, for example, to create a sub-sternal tunnel in which to position a medical device, such as medical electrical lead 16. After making a superficial incision, an operator, using tools and techniques known to those skilled in the art, may open a passageway between diaphragmatic attachments 18 and diaphragm 19, for example, by blunt dissection, in which the operator may employ a tunneling tool, for example, the Medtronic® Model 6996T, to both create the passageway and then form a sub-sternal tunnel (e.g. along the dotted line of FIG. 2). However, because the bony structure of the sternum inhibits external palpation, the operator must take extra care, during the blunt dissection and/or tunneling, not to injure sub-sternal structures or the chest cavity, which could compromise the pleura 39 of the lungs or the heart 6. Thus, as indicated above, tools and associated methods disclosed herein are configured to help an operator gain the desired sub-sternal access and create a space in which to position a medical device, such as medical electrical lead 16, in a more controlled fashion that mitigates the risk of injuring bodily organs.

Figure 3A:
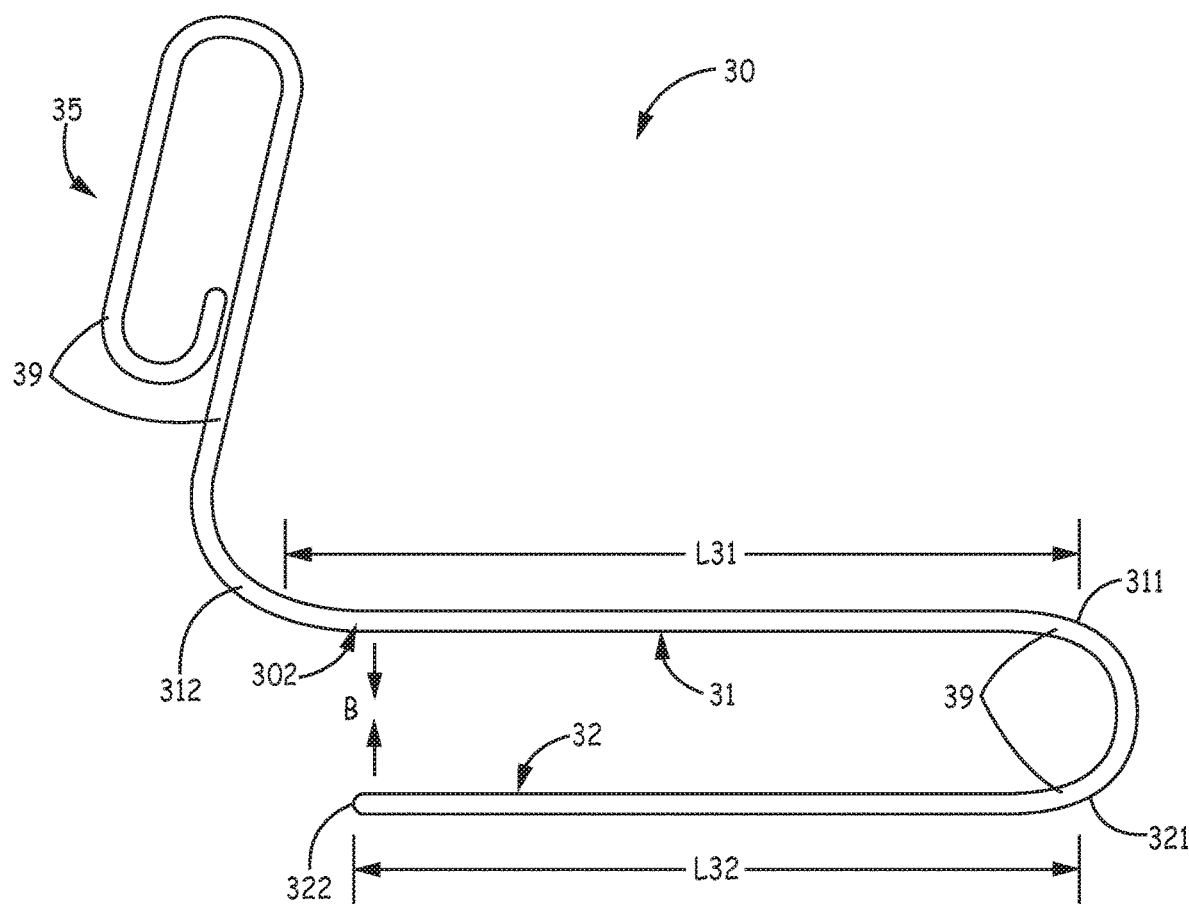
FIG. 3A is a plan view of an example tool for tunneling within a patient.

FIG. 3A is a plan view of a tool 30 for gaining sub-sternal access and creating a sub-sternal tunnel in a patient, according to some embodiments. FIG. 3A illustrates tool 30 including a relatively straight guide member 31 and a tunneling member 32, which are joined together at first ends 311, 321 thereof. Guide member 31 is shown extending over a length L31, from first end 311 to a second end thereof 312. Tunneling member 32 is shown extending, in the same direction, over a length L32, from first end 321 to a blunt tip 322 thereof. Tool 30 also includes a handle 35, which is shown coupled to second end 312 of guide member 31. According to the illustrated embodiment, handle 35, guide member 31, and tunneling member 32 are all formed from a single rod 39, for example, a relatively rigid medical grade polymer rod or a medical grade metal rod. In one example, rod 39 may be formed of 300 series stainless steel having a circular cross-section, which may have a diameter in the range from approximately 0.1 inch (2.5 mm) to approximately 0.14 inch (3.5 mm), for example, approximately 0.12 inch (3.1 mm). According to some embodiments, blunt tip 322 of tunneling member 32 and second end 312 of guide member 31 are biased toward one another, as indicated by arrows B, for example, by an elasticity of rod 39. In other examples, tool 30 may be formed from multiple components, wherein guide member 31 may be biased toward tunneling member 32, and/or tunneling member 32 may be biased toward guide member 31. Furthermore, one or both of guide member 31 and tunneling member 32 may have a non-circular cross-section, in some alternate embodiments.

Figure 3B:
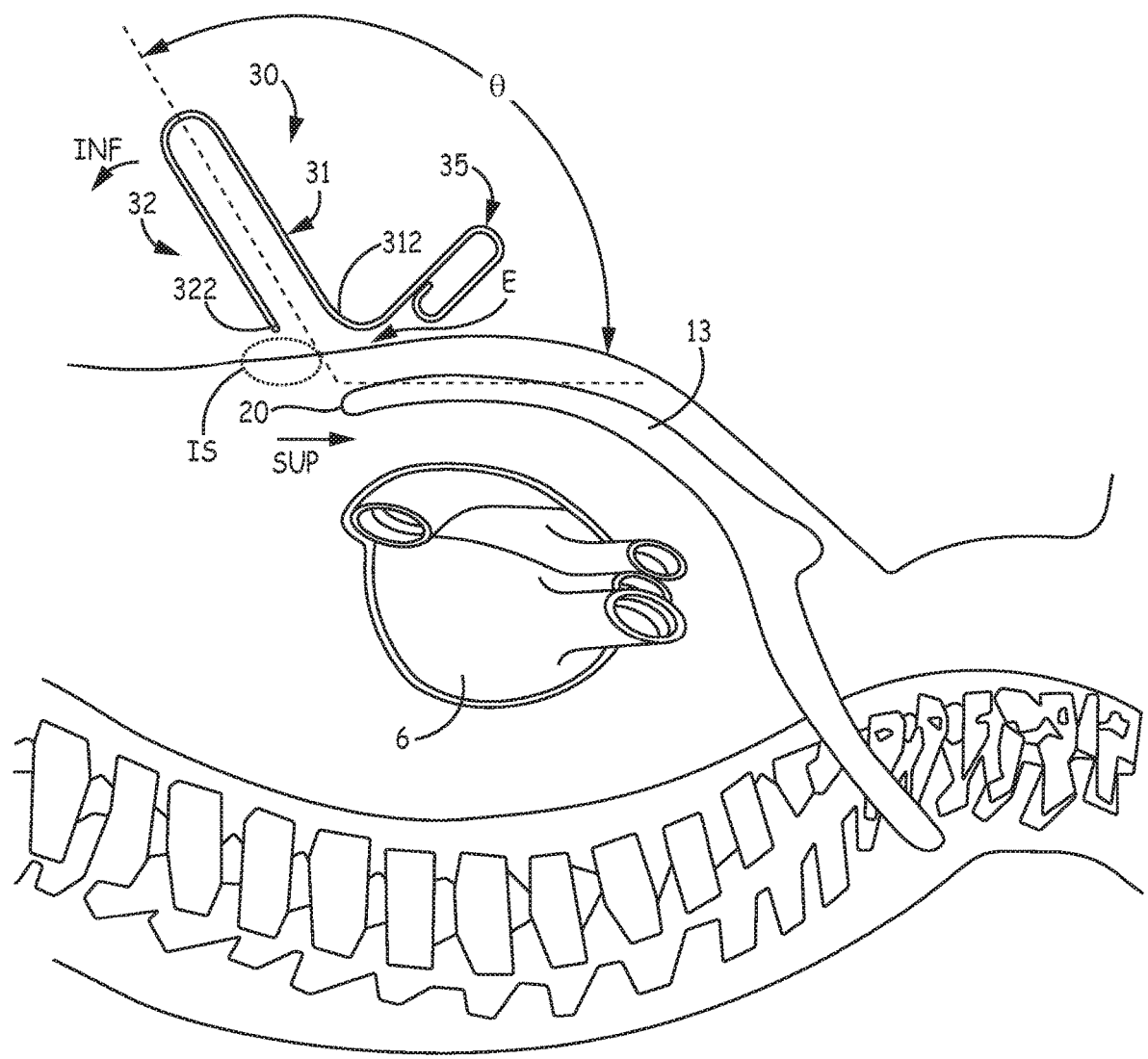
FIG. 3B is a schematic depicting the tool of FIG. 3A positioned for insertion into a body of a patient.

In the example of FIG. 3A, length L32 of tunneling member 32 is less than length L31 of guide member 31. According to the illustrated embodiment, the difference in lengths L31, L32 of guide member 31 and tunneling member 32 is useful to control an angle of entry through an incision site IS of a patient, for example, as illustrated in FIG. 3B. Controlling the angle of entry can mitigate the risk of penetrating too far posterior and injuring sub-sternal structures or the chest cavity. FIG. 3B is a schematic depicting tool 30 positioned for insertion through incision site IS and into a body of a patient. Incision site IS is located in proximity to xiphoid process 20 of sternum 13, for the above-described access to substernal space 3, between diaphragmatic attachments 18 and diaphragm 19 (FIG. 2).

FIG. 3B illustrates guide member 31 and tunneling member 32 of tool 30 oriented at an obtuse angle θ relative to a superior extent of sternum 13 from incision site IS, so that guide member second end 312 will abut a location E, for example, an epidermal location, as the operator inserts blunt tip 322 of tunneling member 32 through incision site IS. With further reference to FIG. 3B, the configuration of tool 30 forces the operator to rotate tunneling member 32 and guide member 31 in an inferior direction, per arrow INF, in order to insert tunneling member blunt tip 322 through incision site IS, thereby keeping the operator from pushing blunt tip 322 too deep or in a wrong direction. According to an alternative exemplary embodiment, tunneling member length L32 may be approximately equal to guide member length L31, in which case, the operator need not orient tool 30 at obtuse angle θ for second end 312 to abut location E, but rather approximately orthogonal to the superior extent of sternum 13 from xiphoid process 20, prior to rotating tool 30 in the inferior direction to insert blunt tip 322 through incision site IS.

Figure 3C:
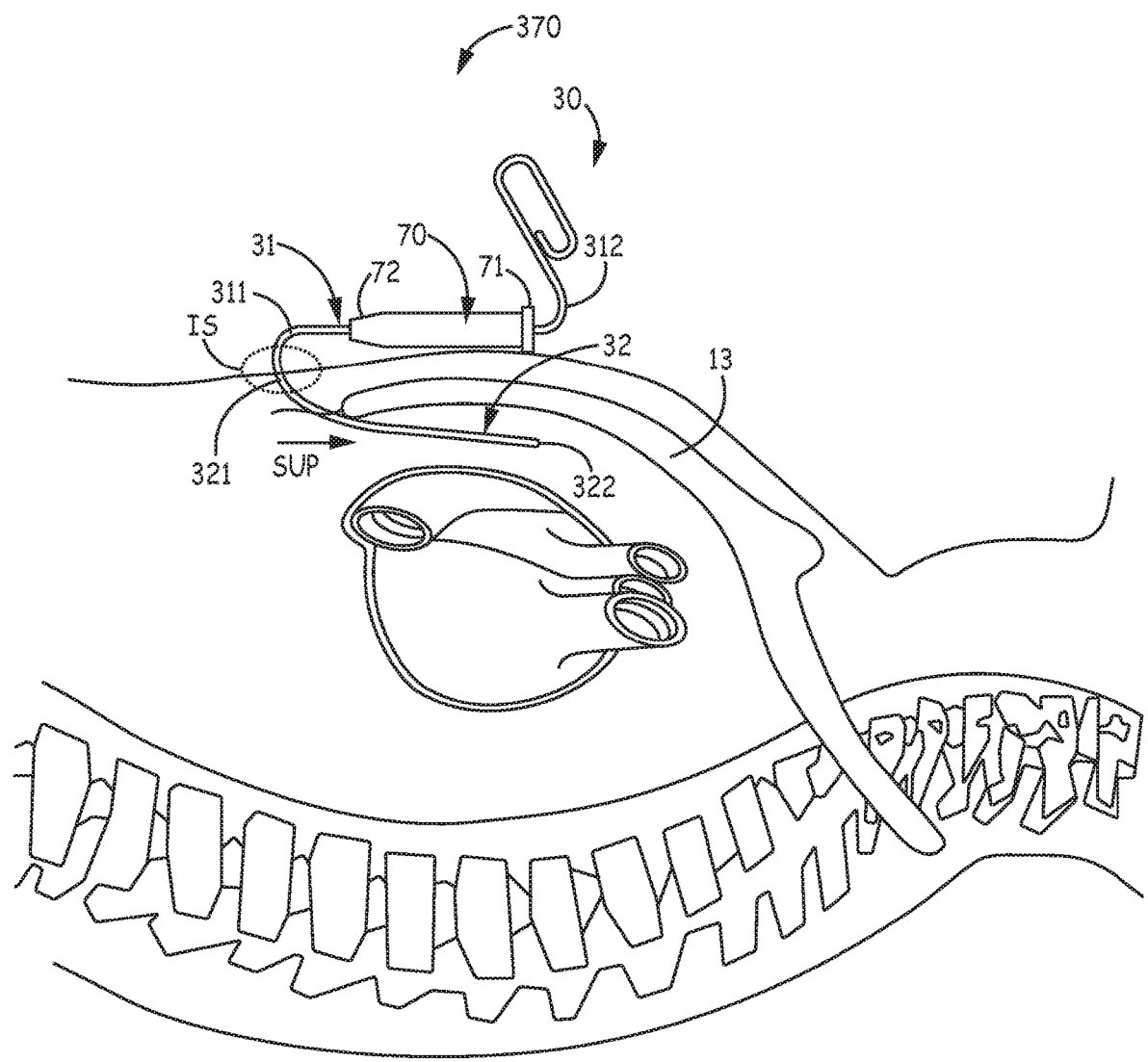
FIG. 3C is a schematic depicting the tool of FIG. 3A, according to some embodiments and methods, advanced superiorly beneath a sternum of the patient.

Furthermore, FIG. 3C shows the extent of guide member 31 aligned along sternum 13, outside the patient's body, to help the operator in advancing tunneling member 32, once tip 322 is inserted, in a proper superior direction, per arrow SUP, and thereby creating the sub-sternal tunnel. According to some embodiments, the bias of blunt tip 322 toward guide member 31 can cause blunt tip 322 to 'ride' adjacent an inside surface of sternum 13 during the superior advancement thereof as an additional aid to the operator. Likewise, second end 312 of guide member 31 may in some instances be rounded such that it easily slides over the skin without poking while traversing in the superior direction. With further reference to FIG. 3C, superior advancement of tunneling member 32 beneath sternum 13 may be stopped when the joined first ends 311, 321 of guide and tunneling members 31, 32 abut incision site IS. Alternately, or in addition, with reference back to FIG. 3A, tool 30 may include an optional marker at a location 302 on guide member 31 that is approximately aligned with blunt tip 322 of tunneling member 32 to provide an indicator that the operator may reference relative to external landmarks of the patient's body to determine the position of tip 322 beneath sternum 13 and thus stop superior advancement at a desired sub-sternal location. However, according to some embodiments and methods, tunneling member 32 and either all or just the marker of guide member 31 are radiopaque, and the operator uses fluoroscopy to monitor the relative locations of tunneling and guide members 32, 31 while advancing blunt tip 322 beneath sternum 13.

FIG. 3C shows tool 30 as part of a system 370 that also includes an introducer sheath 70, according to some embodiments, wherein sheath 70 includes a lumen (not shown). The lumen of sheath 70 includes a proximal opening located at a proximal end 71 of sheath 70, and a distal opening located at a distal end 72 of sheath, and is sized to receive passage of a medical device therethrough, for example, lead 16 (FIGS. 1A-B). FIG. 3C illustrates introducer sheath 70 mounted on tool guide member 31, for example, having been mounted prior to insertion and advancement of tunneling member 32. According to the illustrated embodiment, sheath 70 is configured to slideably engage with guide member 31 and tunneling member 32, and has a flexibility to track around the bend of tool 30 that joins first ends 311, 321 of the guide and tunneling members 31, 32 together, so that, once the operator has advanced tunneling member 32, as shown, to create the sub-sternal tunnel, the operator can slide sheath 70 through incision site IS and along tunneling member 32 into the tunnel, while leaving sheath proximal end 71 external at incision site IS. Then, for example, after tool 30 is withdrawn from the patient's body, leaving sheath 70 within the sub-sternal tunnel, the operator may pass a medical device, such as the above described lead 16, through the sheath lumen, via the proximal opening thereof at sheath proximal end 71. The operator then removes sheath 70 from the body, leaving lead 16 within the sub-sternal tunnel, for example, by slitting or splitting sheath 70 from around lead, according to some embodiments and methods.

In alternative system embodiments, sheath 70 may include an open channel that extends alongside the lumen thereof and that allows for sheath 70 to slideably engage with tunneling member 32, from tunneling member first end 321 in proximity to incision site IS, after tunneling member 32 has created the sub-sternal tunnel. An example of an open channel sheath is described in detail in commonly assigned United States Patent Application No. 2015/0133953, which is incorporated by reference, in its entirety, herein. Such a sheath need not be passed around the bend of tool 30, from guide member 31 to tunneling member 32. Alternately, sheath 70 may be mounted on tunneling member 32 prior to the insertion of tunneling member tip 322 through incision site IS such that sheath 70 is maneuvered and advanced along with tunneling member 32 as the sub-sternal tunnel is created. Furthermore, according to some alternate methods, sheath 70 may be inserted into the sub-sternal tunnel after tool 30 is removed from the patient's body, or the medical device may be inserted into the tunnel without need for any sheath.

Figure 4A:
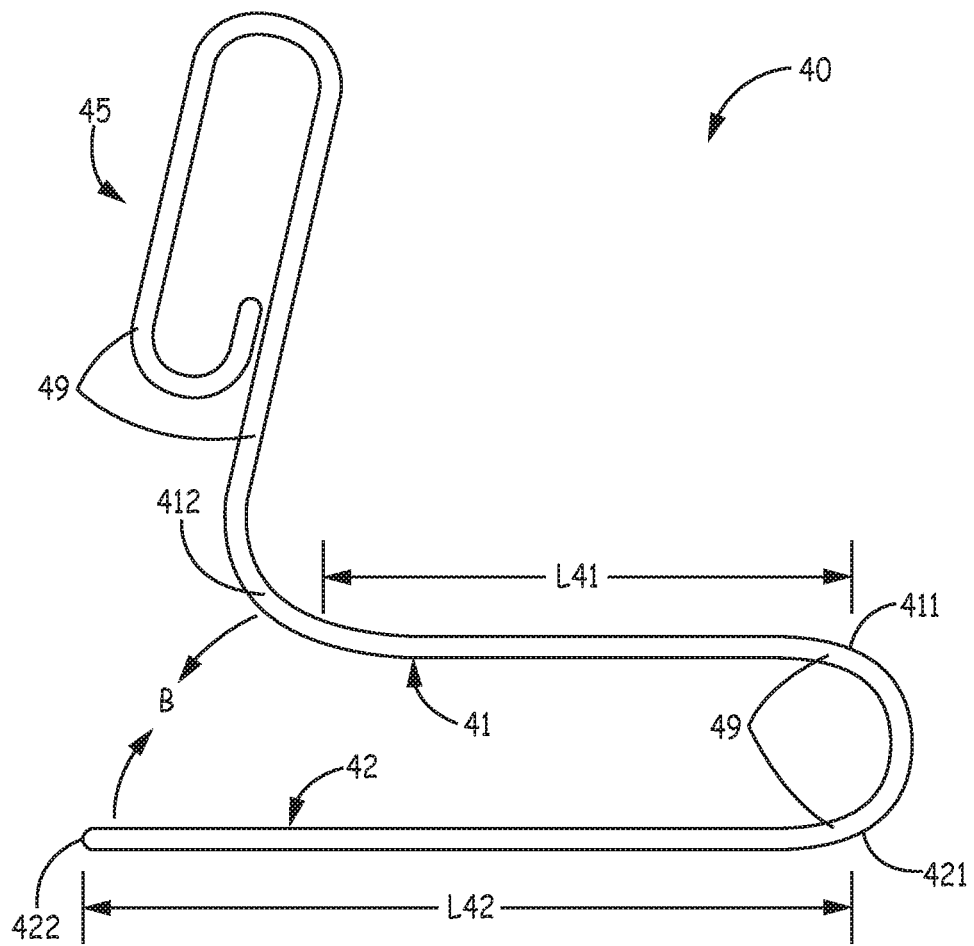
FIG. 4A is a plan view of another example tool for tunneling within a patient.

FIG. 4A is a plan view of a tool 40, according to an alternate embodiment. FIG. 4A illustrates tool 40, like tool 30, including a relatively straight guide member 41 and a tunneling member 42, which are joined together at first ends 411, 421 thereof, and wherein guide and tunneling members 41, 42 extend from respective first ends 411, 421 in the same direction, alongside and coplanar with one another. Also like tool 30, tunneling member 42 includes a blunt tip 422, a handle 45 joined to a second end 412 of guide member 41, and handle 45, guide member 41, and tunneling member 42 are all formed from a single rod 49. Rod 49 may, for example, be a medical grade stainless steel rod like rod 39 of tool 30, described above. According to some embodiments, blunt tip 422 of tunneling member 42 and second end 412 of guide member 41 are biased toward one another, as indicated by arrows B, for example, by an elasticity of rod 49. In other examples, tool 40 may be formed from multiple components, wherein guide member 41 may be biased toward tunneling member 42, and/or tunneling member 42 may be biased toward guide member 41. Furthermore, one or both of guide member 41 and tunneling member 42 may have a non-circular cross-section in some alternate embodiments.

Figure 4B:
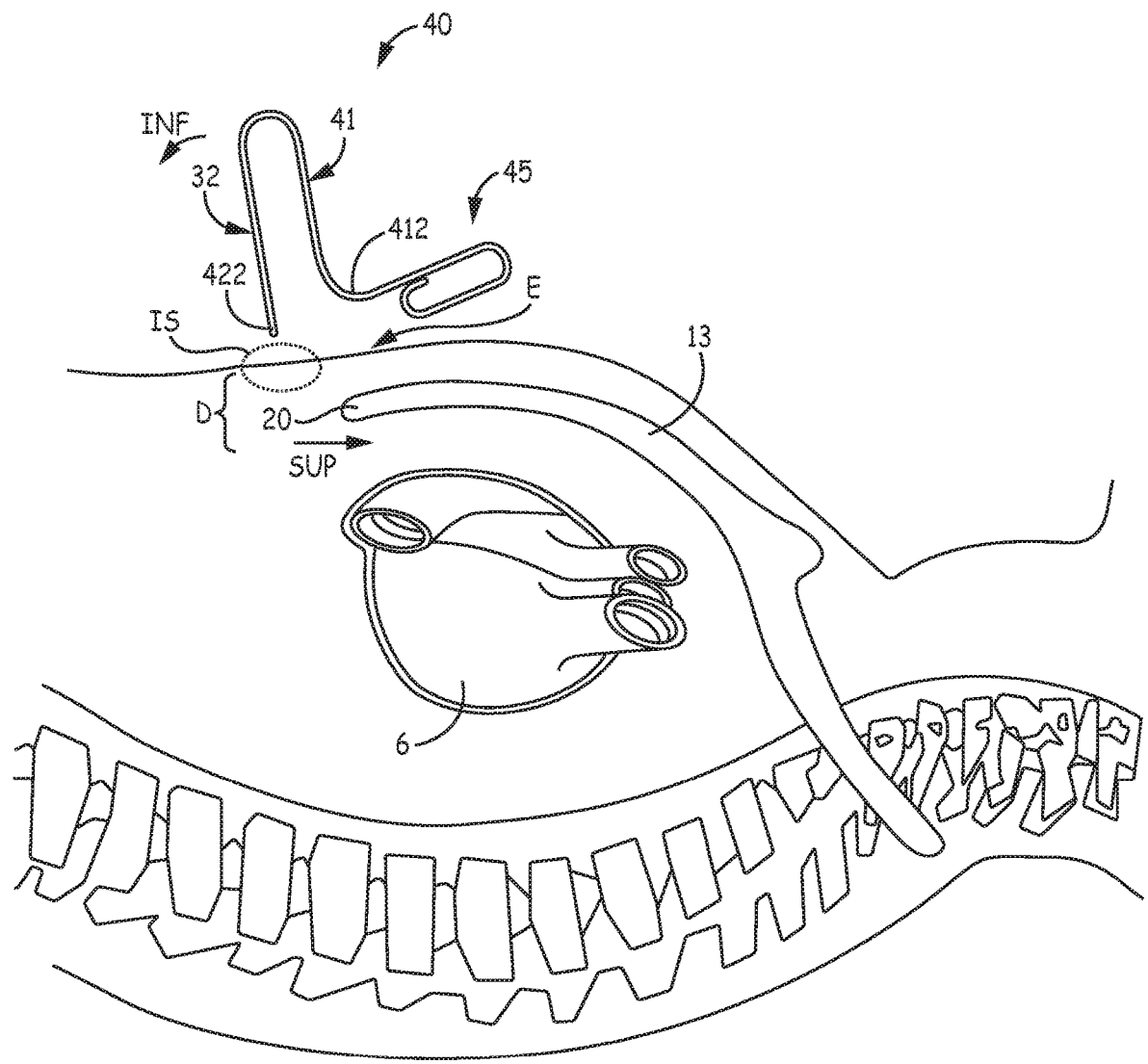
FIG. 4B is a schematic depicting the tool of FIG. 4A positioned for insertion into the body of the patient.
Figure 4C:
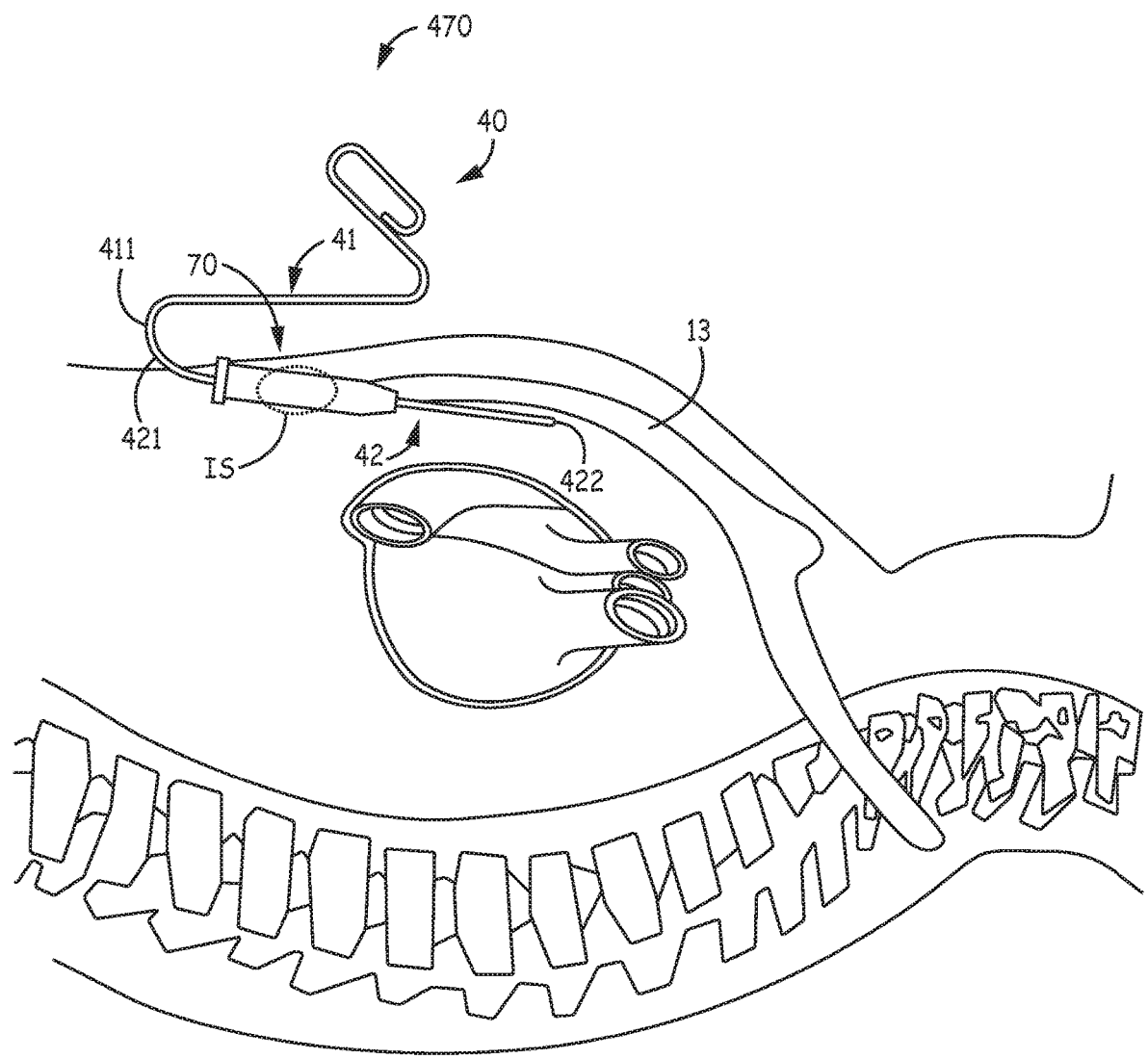
FIG. 4C is a schematic depicting the tool of FIG. 4A, according to some embodiments and methods, advanced superiorly beneath a sternum of the patient.

With further reference to FIG. 4A, tool 40 differs from tool 30 in that a length L42 of tunneling member 42, from first end 421 to tip 422, is greater than a length L41 of guide member 41, from first end 411 to second end 412. According to the illustrated embodiment, the second end 412 of guide member 41 is useful to control a depth of insertion of tunneling member 42 through incision site IS and into the patient's body, for example as described in conjunction with FIG. 4B. FIG. 4B is a schematic depicting tool 40 positioned for insertion through incision site IS. FIG. 4B illustrates tool 40 oriented such that blunt tip 422 of tunneling member 42 is adjacent incision site IS, and guide and tunneling members 41, 42 are approximately orthogonal with respect to the superior extent of sternum 13 from xiphoid process 20. Thus, when the operator inserts blunt tip 422 through incision site IS, second end 412 of guide member 41 (and/or handle 45) serves as a stop, by abutting a location E adjacent incision site IS. This stop can prevent the operator from inserting tip 422 any deeper than a depth D necessary to gain sub-sternal access, and thereby reduce the likelihood of any traumatic injury to bodily organs. Thus, it may be appreciated that tunneling member length L42 is greater than guide member length L41 by no more than depth D, according to some exemplary embodiments, wherein depth D may be between approximately 0.75 inch and approximately 2.25 inch, depending upon the size of the patient. After reaching depth D, the operator may rotate guide member 41 and tunneling member 42 together in the inferior direction, per arrow INF, before advancing tunneling member 42 in the superior direction, per arrow SUP, as is shown in FIG. 4C. It should be noted that the initial orthogonal orientation of tool 40, which allows for insertion to depth D, is not necessary, and the operator, according to some alternate methods may initially orient tool at an obtuse angle similar to angle θ of FIG. 3B. Regardless of orientation, the configuration of tool 40 limits a maximum depth of insertion to reduce the likelihood of trauma while passing through the diaphragmatic attachments to access the substernal space.

Like guide member 31 of tool 30, the extent of guide member 41, being aligned along sternum 13, outside the patient's body, can help the operator to advance tunneling member 42, once tip 422 is inserted, in a proper superior direction, per arrow SUP, to create the sub-sternal tunnel. According to some embodiments, the bias of blunt tip 422 toward guide member 41 can cause blunt tip 422 to 'ride' adjacent an inside surface of sternum 13 during the superior advancement thereof, as an additional aid to the operator. Likewise, second end 412 of guide member 31 may in some instances be rounded such that it easily slides over the skin without poking while traversing in the superior direction. With further reference to FIG. 4C, superior advancement of tunneling member 42 beneath sternum 13 may be stopped by the joined first ends 411, 421 of guide and tunneling members 41, 42 abutting incision site IS. Furthermore, the operator may employ fluoroscopy as described above in conjunction with FIG. 3C.

FIG. 4C further illustrates a system 470 that includes introducer sheath 70 and tool 40, wherein an overall length of sheath 70 is less than length L42 of tunneling member 42, according to some embodiments. FIG. 4C shows sheath 70 having been mounted on tunneling member 42 prior to insertion and advancement of tunneling member 42, such that sheath 70 passes into the sub-sternal tunnel as the tunneling is being created by tunneling member 42, according to some methods. After creating the sub-sternal tunnel, the operator may withdraw tool 40 from the patient's body and leave introducer sheath in place to receive passage of a medical device therethrough and into the tunnel. Of course any of the above-described alternative methods for positioning the sheath and/or medical device in the tunnel may be employed.

Figure 5A:
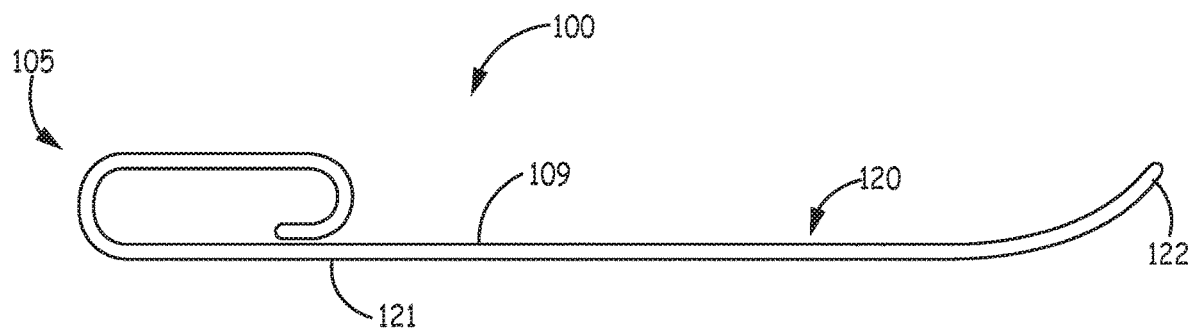
FIG. 5A is a plan view of an exemplary tunneling tool that may be known to those skilled in the art.
Figure 5B:
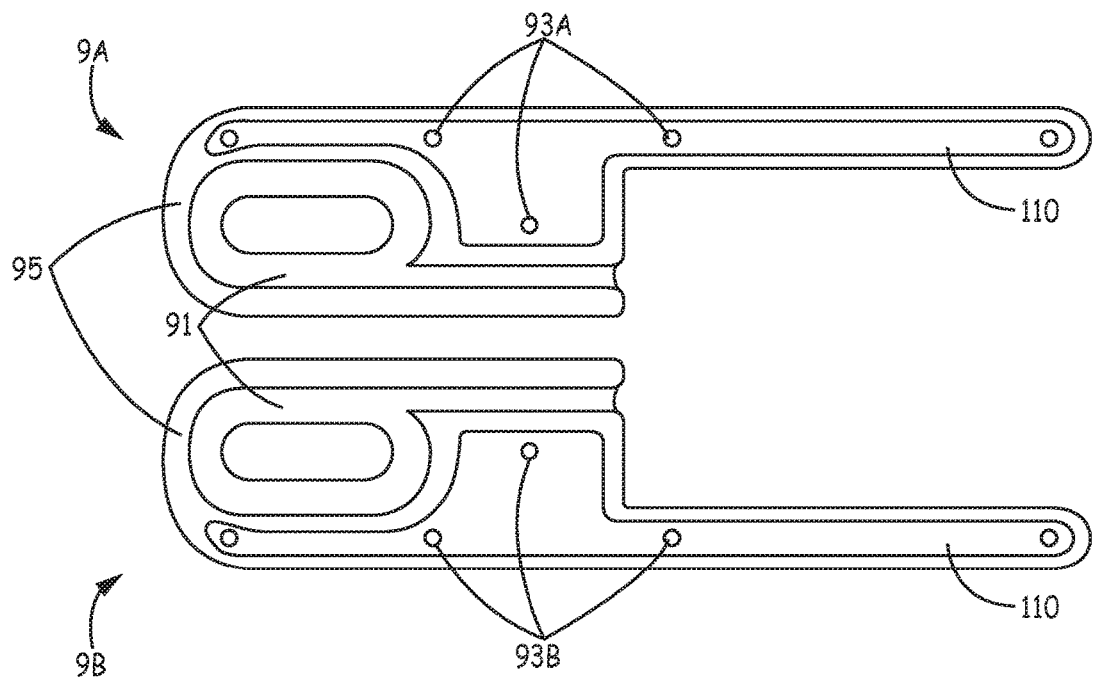
FIG. 5B is a plan view of mating parts of a handle for the tunneling tool of FIG. 5A, according to some embodiments.

FIG. 5A is a plan view of another exemplary tunneling tool 100, which may be formed from an elongate rod 109. Rod 109 may be a medical grade stainless steel rod, for example, like rod 39 of tool 30 described above. FIG. 5A illustrates tool 100 including a handle portion 105 and a tunneling member 120 terminated by a blunt tip 122. In one example, the configuration of tool 100 may substantially conform to that of the Medtronic® Model 6996T tunnel tool. With reference to FIG. 5B, tool 100 can be converted to one that also includes a guide member, for example, by joining parts 9A, 9B together around handle portion 105 and a first end 121 of tunneling member 120. FIG. 5B is a plan view showing mating surfaces of parts 9A, 9B, wherein each includes a channel 91 configured to receive handle portion 105 and tunneling member first end 121 of tool 100. Channels 91 act as an attachment feature that secures parts 9A, 9B to tool 100 when mating features 93A, 93B of the opposing surfaces are brought together in confronting engagement for a snap fit around tool 100. It should be noted that parts 9A, 9B may include any other suitable type of attachment feature to secure tool 100 thereto, as well as any suitable type of mating features to secure parts 9A, 9B together around tool 100. Parts 9A, 9B may be formed, for example, by injection molding, from a relatively hard medical grade polymer.

Figure 5C:
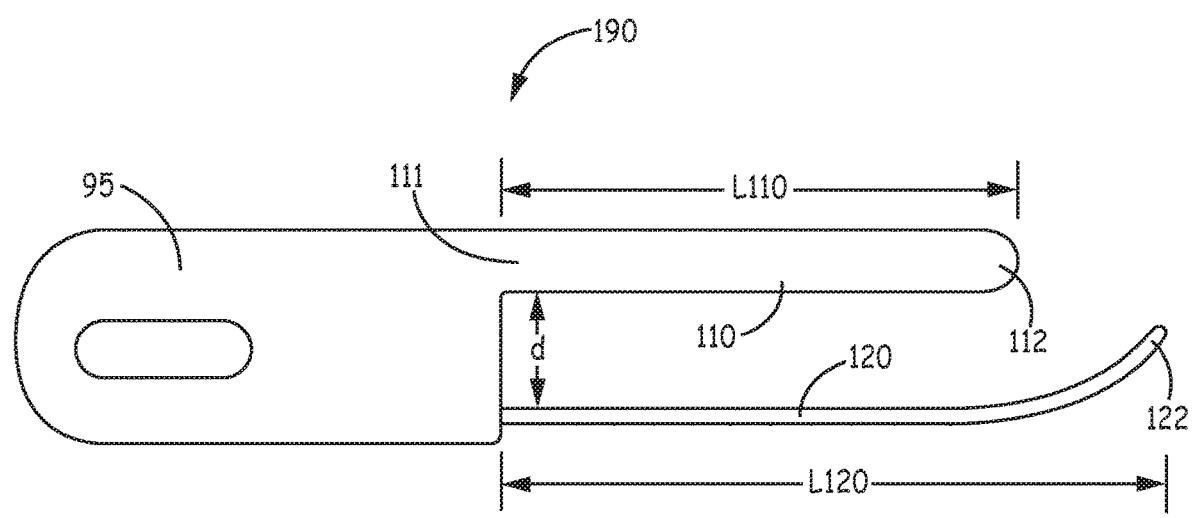
FIG. 5C is a plan view of the parts of FIG. 5B joined to the tool of FIG. 5A, according to some embodiments.

FIG. 5C is a plan view of tool 100 having thus been converted with parts 9A, 9B to a tool 190, wherein tool 190 includes a relatively straight guide member 110 extending from a first end 111 thereof to a second end 112 thereof, alongside tunneling member 120. Second end 112 of guide member 110 may in some instances have a curvature such that it should ride on the skin over the sternum without binding on the skin. For example, second end 112 may be rounded enough to easily slide over the skin without poking. FIG. 5C illustrates a handle 95 of tool 190, which is formed by the portions of parts 9A, 9B surrounding handle portion 105 of tool 100. According to the illustrated embodiment, handle 95 has a looped gripping portion, for example, to receive fingers of a hand of an operator, but may have any other suitable configuration for gripping, such as is described for alternate tool embodiments herein, or known in the art. In contrast to the above-described tools 30 and 40, handle 95 is coupled to first end 111 of guide member 110 and to first end 121 of tunneling member 120, rather than being coupled only to guide member 110. However, the operator may orient tunneling member 120 in a similar fashion to that shown for tool 40 in FIG. 4B to insert blunt tip 122 of tunneling member 120 through incision site IS. Although a length L120 of tunneling member 120 is shown being greater than a length L110 of guide member 110, for example, by no more than the above-described depth D (FIG. 4B), in some alternate embodiments, length L120 may be equal to or less than length L110. In any case, guide member 110, being co-planar with tunneling member 120, provides an external reference to help the operator advance the inserted blunt tip 122 of tunneling member 120 in the proper superior direction to create the sub-sternal tunnel as described above in conjunction with FIGS. 3C and 4C. According to some embodiments, an implant system includes tool 190 and an introducer sheath, for example, similar to any of the embodiments of introducer sheath 70 described above. The sheath may be placed over tunneling member 120 either before or after accessing and tunneling through the sub-sternal space.

Figure 6D:
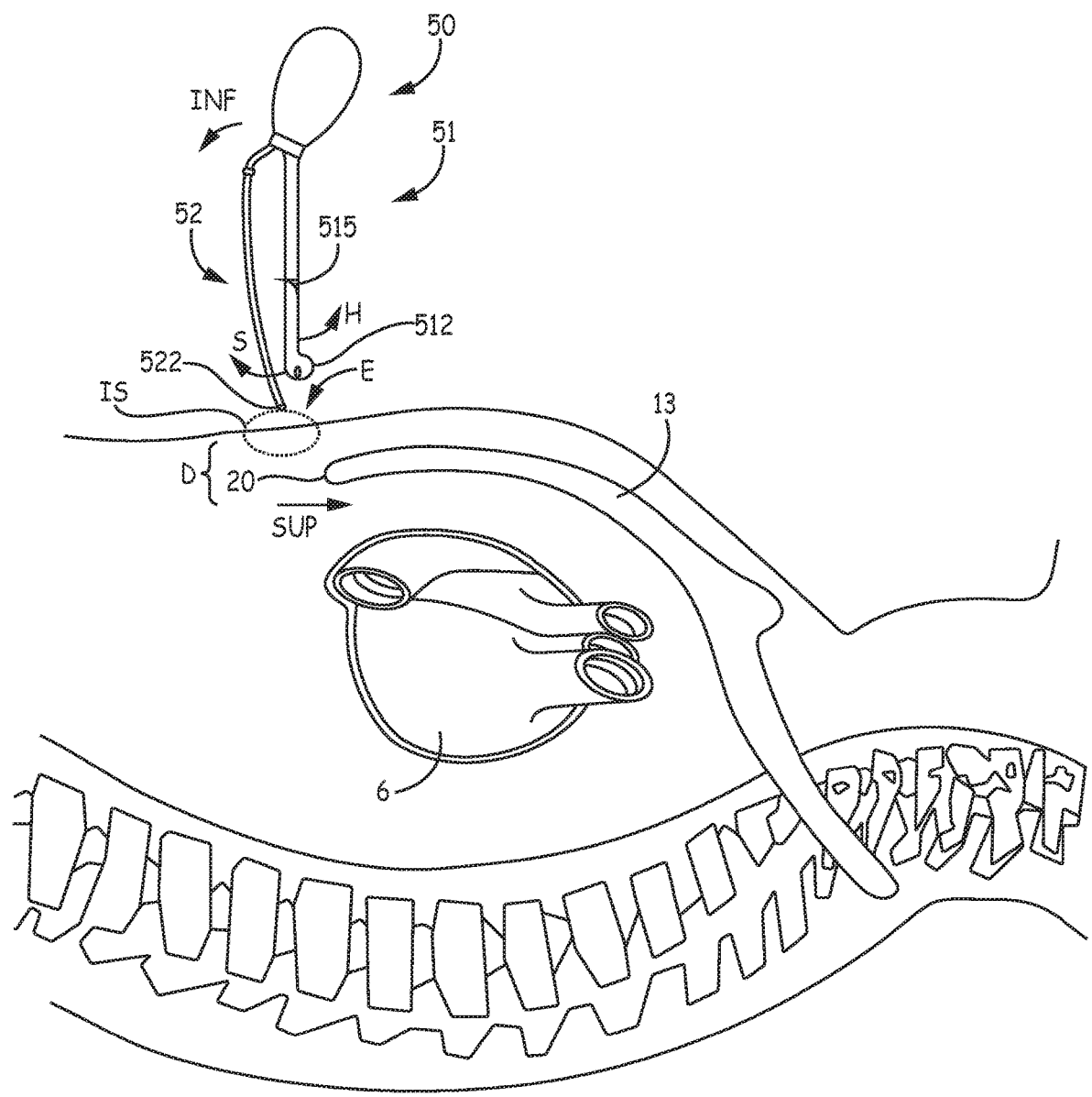
FIG. 6D is a schematic depicting the tool of FIGS. 6A-C positioned for insertion into the body of the patient.

FIGS. 6A-C are a plan view, a corresponding end view, and top view of a tool 50, according to some additional embodiments. FIGS. 6A-C illustrate tool 50 including a relatively straight guide member 51 and a tunneling member 52 that extend in the same direction from first ends 511, 521 thereof, alongside and coplanar with one another. A handle 55 of tool 50 is shown being coupled to first ends 511, 521 of guide and tunneling members 51, 52, and extending at an angle β with respect to the relatively straight extent of guide member 51, wherein angle β may be between approximately 150 degrees and 160 degrees, and is coplanar with guide and tunneling members 51, 52. FIGS. 6A-C further illustrate a length L52 of tunneling member 52, from first end 521 to a blunt tip 522 thereof, being greater than a length L51 of guide member 51, from first end 511 to a second end 512 thereof, but, with reference to FIG. 6D, by no more than the above-described depth D of insertion so that guide member second end 512 will abut location E adjacent incision site IS when tip 522 reaches depth D. According to an exemplary embodiment, guide member length L51 may be approximately 6 inches (15.2 cm), and tunneling member length L52 may be approximately 7 inches (17.8 cm). According to some alternate embodiments, tunneling member length L52 may be approximately equal to, or less than guide member length L51.

According to some exemplary embodiments, tunneling member 52 is formed from a medical grade metal rod, such as a series 300 stainless steel rod having a diameter in a range from approximately 0.1 inch (2.5 mm) to approximately 0.14 inch (3.5 mm), for example, approximately 0.122 inch (3 mm); and handle 55 and guide member 51 are each formed from a relatively hard medical grade polymer. In some alternate embodiments, tunneling member 52 may also be formed from a relatively hard medical grade polymer. Guide member 51 may have a diameter in a range from approximately 0.35 inch (9 mm) to approximately 0.4 inch (10 mm), for example, approximately 0.374 inch (9.5 mm). Handle 55 may be insert molded around first ends 511, 521 of guide and tunneling members 51, 52, or handle 55 and guide member 51 may be integrally formed, for example, by insert molding around first end 521 of tunneling member 52, or handle 55, guide member 51, and tunneling member 52 may each be separately formed and then assembled together. According to the illustrated embodiment, handle 55 has a bulbous contour, for example, with a maximum diameter DH in a range from approximately 1.5 inches to approximately 2.5 inches, for example, approximately 2 inches (51 mm), and length LH in a range from approximately 3 inches to approximately 3.5 inches, for example, approximately 3.25 inches (82.6 mm). The contour and angle β of handle 55 may provide for ergonomic handling of tool 50 that increases an ease of use for the operator, yet other contours and orientations of handle 55 are not outside the scope of the present invention.

Figure 6E:
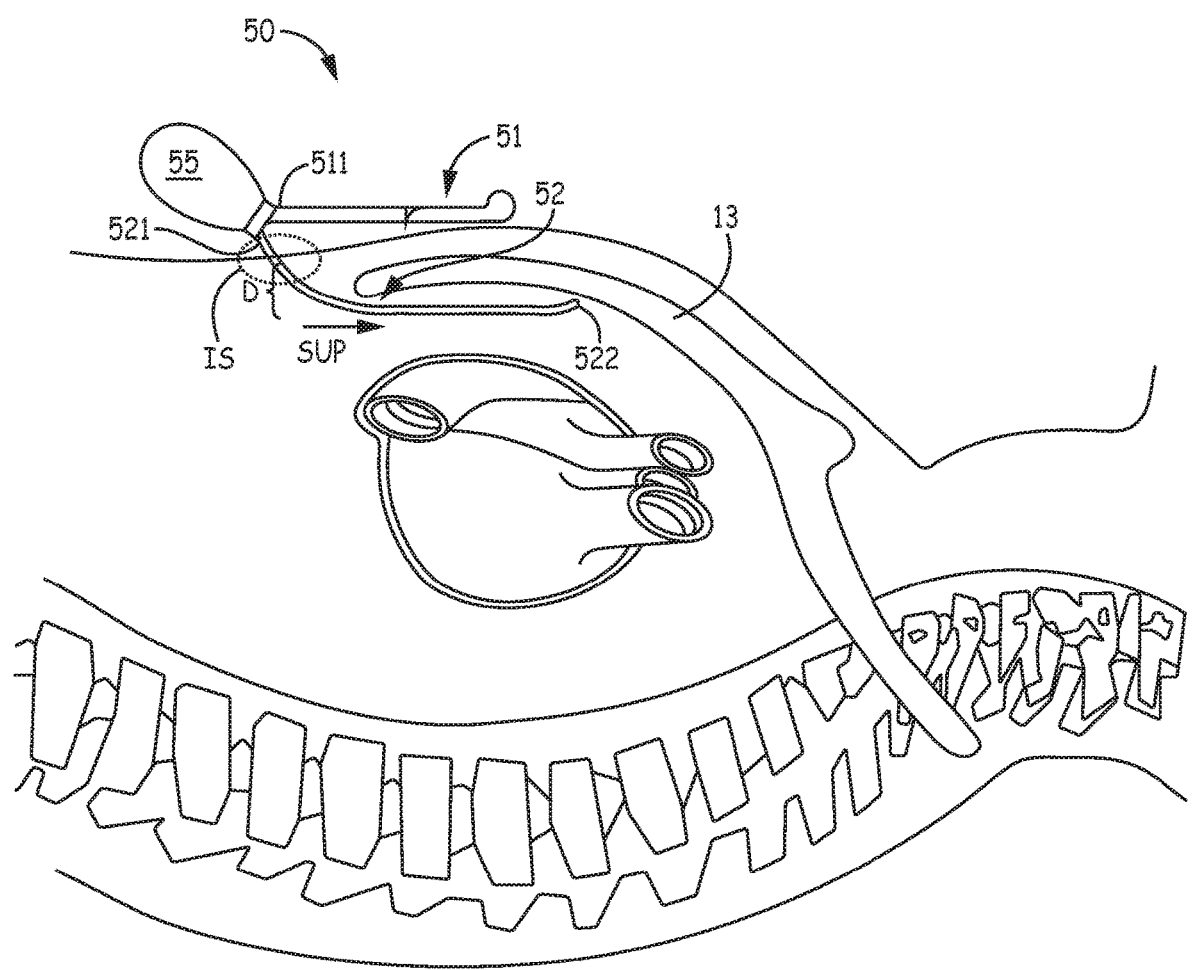
FIG. 6E is a schematic depicting the tool of FIGS. 6A-C, according to some embodiments and methods, advanced superiorly beneath a sternum of the patient.

FIG. 6D illustrates tool 50 oriented such that blunt tip 522 of tunneling member 52 is adjacent incision site IS, and guide and tunneling members 51, 52 are approximately orthogonal with respect to the superior extent of sternum 13 from xiphoid process 20. After reaching depth D, the operator may rotate guide member 51 and tunneling member 52 together in the inferior direction, per arrow INF, before advancing tunneling member 52 in the superior direction, per arrow SUP, as is shown in FIG. 6E. With further reference to FIG. 6A, tunneling member 52 has an elastic property and a pre-formed curvature that bias blunt tip 522 toward second end 512 of guide member 51. FIG. 6A shows a gap g between blunt tip 522 and second end 512 of guide member 51, which may be in a range from approximately 0.2 inch to approximately 0.3 inch, for example, approximately 0.25 inch (6.4 mm), according to some embodiments, when tunneling member 52 is in the relaxed state (e.g. biased toward guide member 51 by the elastic property thereof). Gap g may be increased, for example, per arrow S of FIG. 6D, when the operator inserts and begins to rotate tool 50 in the inferior direction, per arrow INF, to advance tunneling member 52 beneath sternum 13 in the superior direction, per arrow SUP. The bias of tunneling member 51, which seeks to restore gap g, causes blunt tip 522 to 'ride' adjacent the inside surface of sternum 13 during the superior advancement thereof.

FIGS. 6A and 6C also show guide member 51 divided into first and second sections 51A, 51B, which may be joined together by a hinge member 515. Hinge member 515 allows guide member second section 51B to rotate per arrow H, for example, providing additional clearance as the operator inserts and advances tunneling member 52. Hinge member 515 may be constructed in any suitable manner known to those skilled in the art. Some embodiments of hinge member 515 include a torsion spring, while others include a coiled spring member extending around a junction between first and second sections 51A, 51B. According to some alternate embodiments, guide member 51 is not divided into sections 51A, 51B.

With further reference to FIG. 6E, the superior advancement of tunneling member 52 beneath sternum 13 may be stopped by the joined first ends 511, 521 of guide and tunneling members 51, 52 abutting incision site IS. But, with reference back to FIG. 6A, if a distance d between guide member 51 and tunneling member 52, in proximity to first ends 511, 521 thereof, is not sufficient for a size of a given patient (e.g., approximately equal to depth D of the patient), the operator may not be able to advance tunneling member 52 enough to create a sub-sternal tunnel of sufficient length to accommodate the medical device. Conversely, if distance d is too large, a relatively large gap between guide member 51 and the epidermis of the patient may cause a parallax viewing error for the operator monitoring the superior advancement of tunneling member 52 via guide member 51. Thus, according to some embodiments, tool 50 may include an adjustment mechanism to vary distance d. FIG. 6A illustrates one type of adjustment mechanism that is formed by a threaded interface T that couples first end 521 of tunneling member 52 to handle 55. According to the illustrated embodiment, handle 55 may be rotated relative to guide member 51, to adjust distance d, per arrow A, thereby moving tunneling member 52 into multiple positions relative to guide member 51. However, handle 55 may incorporate any other suitable type of adjustment mechanism. Alternately, the adjustment of tool 50 to accommodate different sizes of patients may be accomplished with a kit that includes an assortment of interchangeable tunneling members 52 having shanks S5 of different lengths. Likewise, with reference back to FIG. 5B, a kit may include an assortment of mating parts 9A, 9B of different sizes to vary distance d of tool 190 assembled from tool 100.

According to some methods, the operator may use fluoroscopy to monitor the relative locations of tunneling and guide members 52, 51 while advancing blunt tip 522 beneath sternum 13, as described above for tool 30. Therefore, with further reference to FIG. 6A, tunneling member 52 may be radiopaque and guide member 51 may include a radiopaque marker 502 located in proximity to second end 512. To further assist the operator in maintaining a proper orientation of tunneling member 52, while advancing member 52 beneath sternum 13, FIGS. 6A-C further illustrate guide member 51 including an optional orientation feature 514, which has a fin-like configuration and is joined to second end 512 and extends away from, and coplanar with guide member 51 and tunneling member 52. With reference to FIG. 6B, the operator can observe feature 514 for any tilting, for example, per arrows t, as an indicator that tunneling member 52 has been inadvertently rotated so that curved tip 522 is directed away from the superior direction of the advancement of tunneling member 52. It should be noted that feature 514, in alternate embodiments, may be located in other positions along guide member 51, and/or take on other suitable configurations.

Figure 7A:
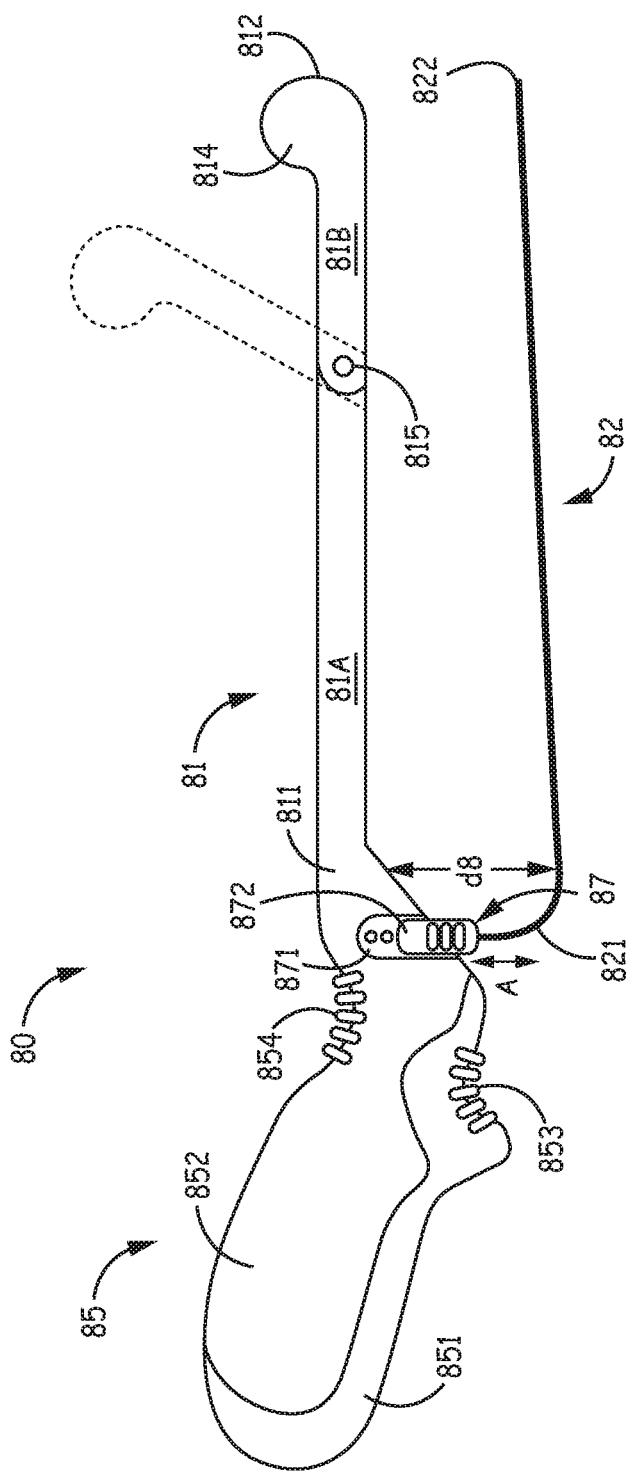
FIG. 7A is a plan view of a tool, according to some alternate embodiments.

FIG. 7A is a plan view of a tool 80, according to some alternate embodiments. FIG. 7A illustrates tool 80 including a relatively straight guide member 81 and a tunneling member 82 that extend in the same direction from first ends 811, 821 thereof, alongside and coplanar with one another. A length of tunneling member 82, from first end 821 to a blunt tip 822 thereof, is shown being approximately equal to a length of guide member from first end 811 to a second end 812 thereof. Like guide member 51 of tool 50, guide member 81 may be formed from a medical grade polymer, and may include an optional orientation fin 814. FIG. 7A further illustrates a handle 85 of tool 80 being coupled to first ends 811, 821 of guide and tunneling members 81, 82. Handle 85 includes first and second finger recesses 853, 854, which are shown located in proximity to guide and tunneling member first ends 811, 821, and an adjustment mechanism 87, which is shown located in proximity to recesses 853, 854. Adjustment mechanism 87 is shown coupling first end 821 of tunneling member 82 to handle 85, wherein a first part 871 of mechanism 87 may be a column of protrusions or recesses configured to interlock with a second part 872 of mechanism 87, for example, a tab member secured to first end 821 of tunneling member 82. According the illustrated embodiment, an operator may move second part 872 of adjustment mechanism 87 over first part 871, per arrow A, to lock tunneling member 82 at different positions relative to guide member 81, and thereby vary a distance d8 between guide member 81 and tunneling member 82, according to different sizes of patients (e.g., different depths D, as described above in conjunction with FIG. 6E). According to an exemplary embodiment, distance d8 may be varied by about 0.5 inch (12.7 mm), wherein a maximum distance d8 may be approximately 2.24 inch (57 mm).

Figure 7B:
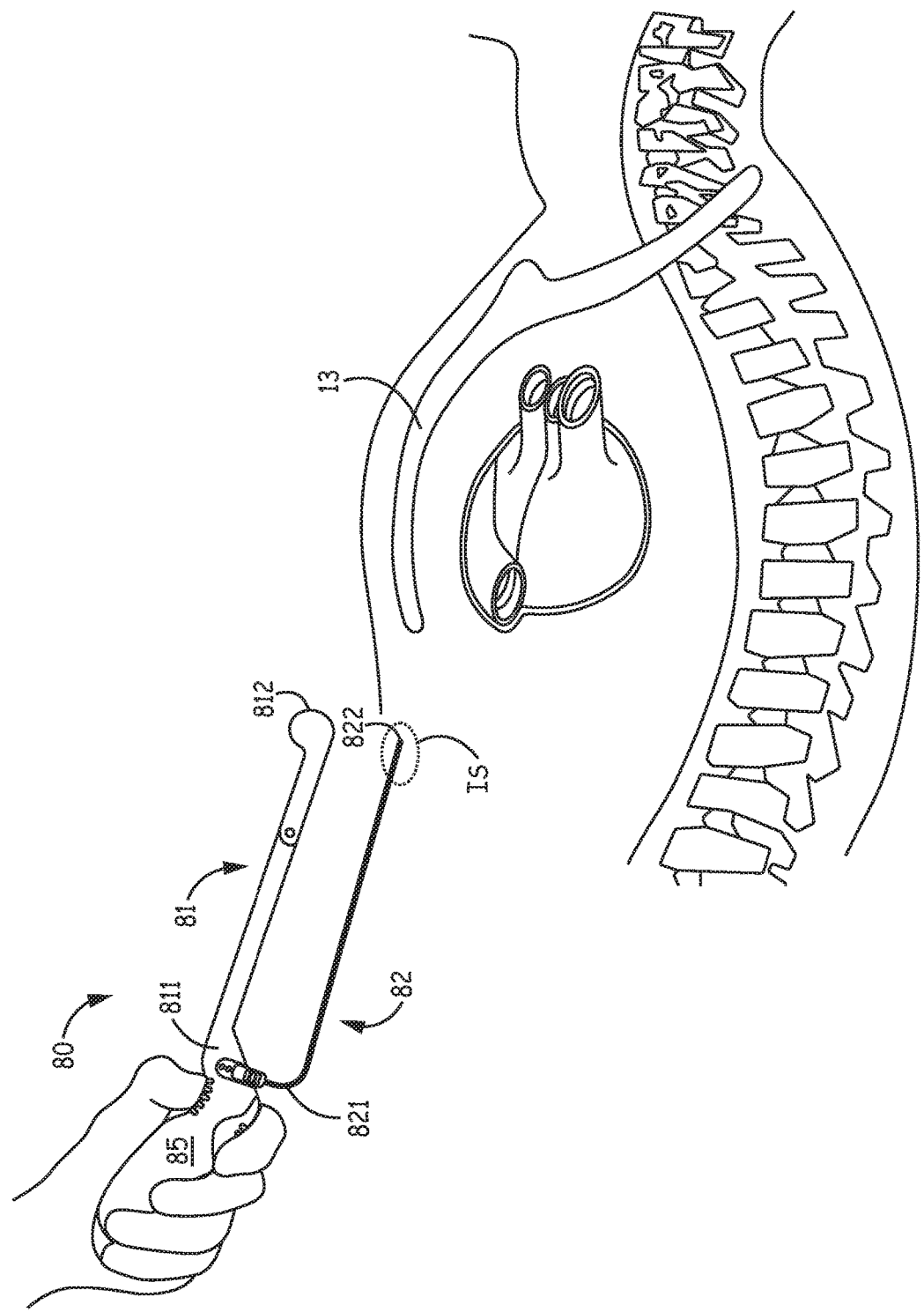
FIGS. 7B-C are schematics depicting handling the tool of FIG. 7A, according to some methods.
Figure 7C:
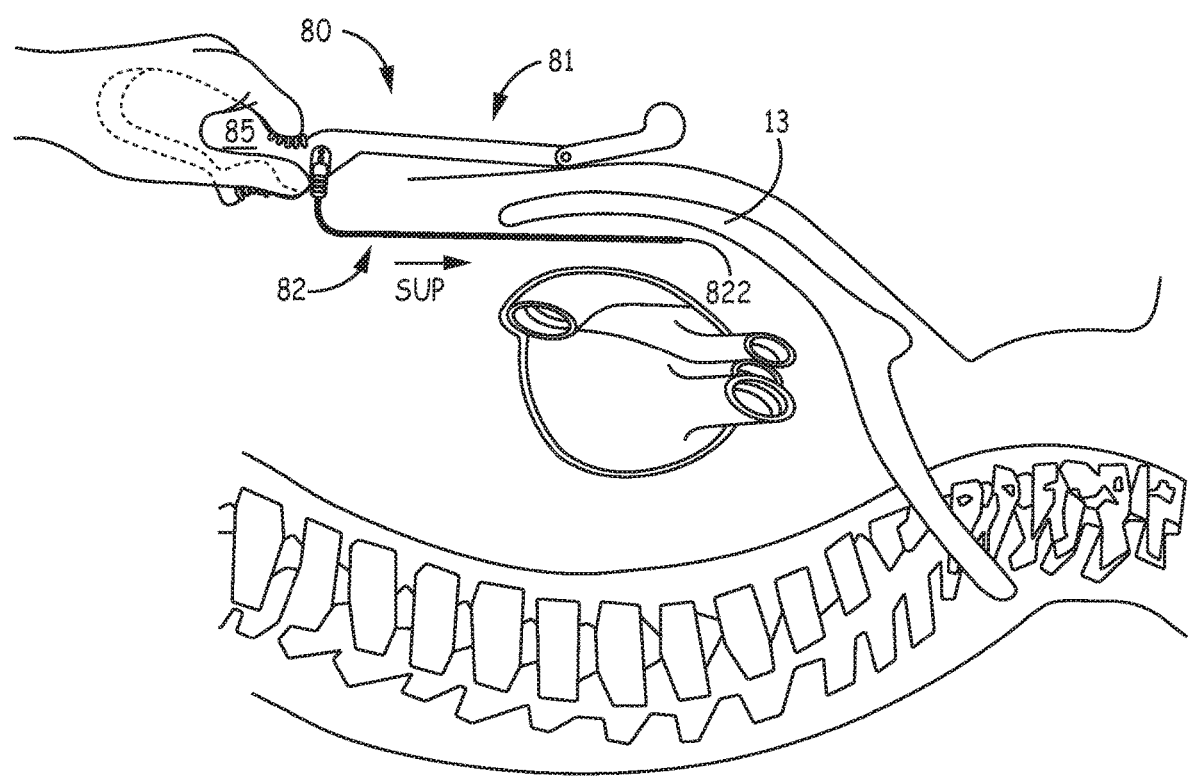

Like handle 55 of tool 50, handle 85 may extend at an angle with respect to the relatively straight extent of guide member 81, which provides some clearance for an operator's hand while handling and manipulating tool 80, for example, as shown in the schematics of FIGS. 7B-C. FIG. 7B shows the operator's hand gripping handle 85 such that a forefinger of the hand rests in first finger recess 853 of handle 85, and a thumb of the hand rests in second finger recess 854 of handle 85. The grip of FIG. 7B may be one suitable for steering blunt tip 822 of tunneling member 82 into incision site IS as shown. FIG. 7C shows the operator's hand gripping handle 85 such that the thumb extends alongside first recess 853 and the forefinger wraps around handle 85 alongside second recess 854. The grip of FIG. 7C may one suitable for advancing the inserted tunneling member 82 in the superior direction to create a sub-sternal tunnel. With further reference to FIG. 7A, handle 85 may be formed by a relatively hard plastic or metal body 852 over-molded with a relatively softer elastomer 851, to enhance gripping, and each recess 853, 854 may have a row of elastomer gripping nubs over-molded thereon.

With further reference to FIG. 7A, guide member 81, like guide member 51 of tool 50, may be divided into first and second sections 81A, 81B, which may be joined together by a hinge member 815, for example, to provide additional clearance as the operator inserts and advances tunneling member 82, by allowing guide member second section 81B to rotate as shown in FIG. 7C and by the dashed lines in FIG. 7A. Hinge member 815 may be constructed in any suitable manner known to those skilled in the art. Some embodiments of hinge member 815 include a torsion spring, while others include a coiled spring member extending around a junction between first and second sections 81A, 81B.

FIG. 8A is a plan view of a tool 60, according to some embodiments; and FIG. 8B is an enlarged detail of a portion of tool 60. FIG. 8A illustrates tool 60 including a relatively straight guide member 61 and a tunneling member 62, wherein guide member 61 extends over a length from a first end 611 thereof to a second end 612 thereof, and tunneling member 62 extends over a length from a first end 621 thereof to a blunt tip 622 thereof. Members 61, 62 extend in the same direction from first ends 611, 621 thereof, alongside and coplanar with one another, and may have lengths and diameters similar to those of the corresponding members 51, 52 of tool 50. According to some alternate embodiments, tunneling member length L62 may be approximately equal to, or less than guide member length L61. Guide member 61 may be formed from a medical grade polymer, and is shown including an optional orientation fin 614, for example, like guide members 51, 81 of tools 50, 80. Dashed lines in FIG. 8A represent an optional metal rod embedded in guide member 61, for example, to lend stiffness and/or radiopacity. FIG. 8A further illustrates a handle 65 of tool 50 coupled to first ends 611, 621 of guide and tunneling members 61, 62, wherein handle 65 may be formed form a relatively hard medical grade plastic, in some cases integrally formed with guide member 61. Handle 65 preferably has an oval cross-section (into the page), and is shown including an optional plurality of finger recesses 653 to conform to a hand of the operator. Dotted lines illustrate an alternate handle embodiment in which handle 65 is angled relative to the extent of guide member 61, for example, like handle 85 of tool 80, to provide some clearance for an operator's hand when handling tool 60 during the tunneling procedure.

With reference to the detail of FIG. 8B, tool 60 further includes a spring-loaded coupling 625 between handle 65 and tunneling member first end 621, which is shrouded within a bulk of handle 65. FIG. 8B illustrates coupling 625 including a spring mechanism 656 and a pivot member 658, wherein spring mechanism 656 is biased in a direction SB1 such that tunneling member 62, rotating around pivot member 658, is biased toward guide member 61, per arrow SB2. With reference back to FIGS. 6D-E, like tool 50, guide member second end 612 of tool 60 may abut location E adjacent incision site IS when an operator has inserted blunt tip 622 to depth D, and, as the operator begins to rotate the inserted tool 60 in the inferior direction, per arrow INF, to advance tunneling member 62 beneath sternum 13 in the superior direction, per arrow SUP, the operator may apply enough force against the spring bias of spring mechanism 656 to allow tunneling member 62 to spread apart from guide member 61, per arrow S (FIG. 8A), but the spring bias of tool 60 can still be sufficient to keep blunt tip 622 riding along the inner surface of sternum 13 during the superior advancement thereof. Furthermore, when tunneling member 62 is radiopaque, and guide member 61 includes a radiopaque member, for example, the rod described above (dashed lines in FIG. 8A), the operator may employ fluoroscopy to monitor the relative locations of tunneling and guide members 62, 61, while advancing blunt tip 622 beneath sternum 13. Additionally, the joined first and second ends 611, 621 of guide and tunneling members 61, 62 can serve to stop the superior advancement of blunt tip.

FIGS. 8C-D are plan views of a variation of tool 60. FIGS. 8C-D illustrate a tool 600 including a relatively straight guide member 601 and a tunneling member 602 that extend alongside and coplanar with one another. Similar to guide and tunneling members 61, 62 of tool 60, guide member 601 extends from a first end 6011 thereof to a second end 6012 thereof, and tunneling member 602 extends from a first end 6021 thereof to a blunt tip 6022 thereof, both in the same direction. FIGS. 8C-D further illustrate a handle 605 of tool 600 coupled to first ends 6011, 6021 of guide and tunneling members 601, 602, wherein handle 605 includes an adjustment mechanism 607 that allows an operator to vary a distance d6 between guide member 601 and tunneling member 602, according to different sizes of patients (e.g., different depths D, as described above in conjunction with FIG. 6E). According to the illustrated embodiment, adjustment mechanism 607 includes a slot (shown with a dotted line) formed in handle 605 to receive a shank S6 of guide member 601, and a set screw 6076 for securing shank S6 in one of a plurality of positions, via one of a plurality of mating apertures 6016 formed in shank S6. FIG. 8C shows set screw 6076 securing shank S6 (shown with dashed lines) to hold guide member 601 in a first position relative to tunneling member 602; and FIG. 8D shows set screw 6076 securing shank S6 to hold guide member 601 in a second position relative to tunneling member 602, at which distance d6 is greater than when held at the first position. Handle 605 may incorporate any other suitable type of adjustment mechanism, according to some alternate embodiments.

With further reference to FIGS. 8C-D, guide member 601 of tool 600 is shown divided into first and second sections 601A, 601B that are joined together by a hinge member 6015, for example, to provide additional clearance as the operator inserts and advances tunneling member 602, by allowing guide member second section 601B to rotate per arrow H6 (FIG. 8C). Hinge member 6015 may be constructed in any suitable manner known to those skilled in the art, and/or described herein, and is shown including a coiled spring member extending thereabout to provide a spring-bias thereto.

Any or all of the above-described tools 50, 80, 60, 600 may be incorporated in a system that also includes an introducer sheath, for example, sheath 70 described above. According to some methods and embodiments, the sheath is mounted on tunneling member 52, 82, 62, 602, prior to the insertion of blunt tip 522, 822, 622, 6022, and advanced along with tunneling member 52, 82, 62, 602 as it creates the sub-sternal tunnel.

FIGS. 9A-B are plan views of a tool 90, according to some additional embodiments. FIGS. 9A-B illustrate tool 90 including a relatively straight guide member 91 and a tunneling member 92 that extend alongside and coplanar with one another, wherein guide member 91 extends from a first end 911 thereof to a second end 912 thereof, and tunneling member 92 extends from a first end 921 thereof to a blunt tip 922 thereof, both in the same direction. Tunneling member 92 is shown including a first section 92A that extends approximately parallel to guide member 91 and a second section 92B that has a pre-formed curvature biasing blunt tip 922 generally toward guide member 91. First section 92A, being a major portion of the tunneling member 92, allows the operator to use guide member 91 as an external visual cue of the angle at which tunneling member 92 extends during the insertion thereof and tunneling therewith, while the curvature of tunneling member second section 92 can cause blunt tip 922 to 'ride' adjacent the inside surface of sternum 13 during the superior advancement thereof when tunneling.

FIGS. 9A-B further illustrate a handle 950 of tool 90 being coupled to first ends 911, 921 of guide and tunneling members 91, 92, and including a looped gripping portion to accommodate various operator hand sizes, with finger recesses 953 formed therein. According to the illustrated embodiment, to adjust tool 90 according to different sizes of patients (e.g., different depths D, as described above in conjunction with FIG. 6E), handle 950 also includes an adjustment mechanism 97 that allows an operator to vary a distance d9 between guide member 91 and tunneling member 92, in proximity to first ends 911, 921 thereof, for example, by sliding guide member 91 relative to tunneling member 92 along a yoke 951 of handle 950. FIG. 9A shows guide member 91 held at a first position relative to tunneling member 92, and FIG. 9B shows guide member 91 held at a second position relative to tunneling member 92, wherein distance d9 at the second position is less than that at the first position.

Figure 9C:
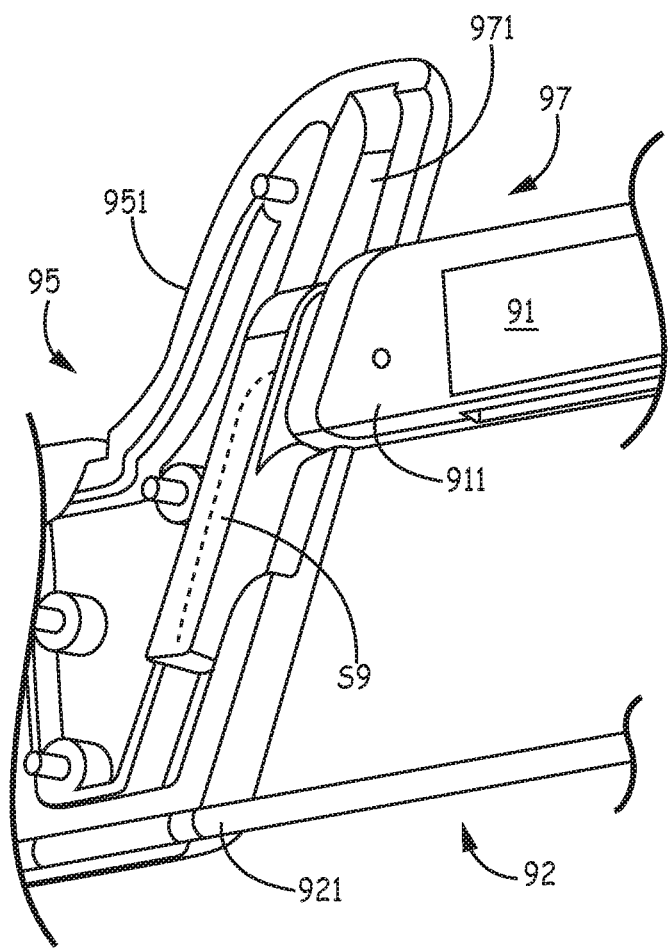
FIG. 9C is an enlarged detail view of a portion of the tool shown in FIGS. 9A-B.

FIG. 9C is an enlarged detail view inside handle yoke 951 that illustrates adjustment mechanism 97 being formed by a shank S9 of guide member 91 mounted in sliding engagement within a slot 971 of yoke 951. In some embodiments, a flat, or leaf spring member (shown with dashed lines) may be mounted to a face of shank S9 and interface with a confronting face of slot 971 to hold guide member 91 in place by preventing guide member 91 from freely sliding within slot 971, while allowing the operator to forcibly slide guide member 91 to various positions. In some alternate embodiments, other suitable interfaces between shank S9 and yoke 951 that prevent the free sliding of guiding member 91 may be employed, for example, ratchet teeth or any other interlocking/detent-type interface. Furthermore, it should be noted that any other suitable coupling between guide member 91 and handle 950, which allows adjustment of distance d9, while maintaining the parallel orientation of guide member 91 relative to tunneling member first section 92A, is not outside the scope of the present disclosure.

With further reference to FIGS. 9A-B, tool 90 also includes an extension tip 93 joined to second end 912 of guide member 91, wherein extension tip 93 is moveable from a retracted position (shown with dotted lines in FIG. 9A) alongside guide member 91 and between the first and second ends 911, 912 thereof, to an extended position, extending away from guide member second end 912. In some embodiments, a pivot joint couples extension tip 93 to second end 912 of guide member 91, while, in alternate embodiments, extension tip 93 is coupled to guide member 91 in a telescoping arrangement. With reference back to FIG. 6D, if the operator initially orients tool 90 in a similar fashion to that illustrated for tool 50, while inserting blunt tip 922 of tunneling member 91 through incision site IS, the operator will likely have extension tip 93 in the retracted position until gaining sub-sternal access. Then, after gaining sub-sternal access, the operator may move tip 93 to the extended position prior to advancing tunneling member 92 in the superior direction (per arrow SUP of FIGS. 6D-E) to create a tunnel. According to the illustrated embodiment, at the extended position, a free end 932 of extension tip 93 is approximately aligned with blunt tip 922 of tunneling member 92, for example, to help the operator understand the sub-sternal location of tip 922 while creating the sub-sternal tunnel. FIGS. 9A-B further illustrate tool 90 including an optional bubble level 914 that can help the operator monitor an orientation of tool with respect to the horizontal during the tunneling procedure.

According to some embodiments, handle 950 of tool 90 includes an attachment feature configured to reversibly secure handle 950 to first end 921 of tunneling member 92 so that tunneling member 92 extends alongside and coplanar with guide member 91, as shown in FIGS. 9A-B. Once the sub-sternal tunnel is created, the attachment feature allows detachment of tunneling member 92 from handle 950, for example, to allow passage of the introducer sheath over tunneling member 92 and into the sub-sternal tunnel, so that the sheath does not need to be pre-loaded around member 92, in contrast to some instances described above for some other tool embodiments. FIGS. 9A-B illustrate a lever 952 of the attachment feature, which, when lifted, or rotated, per arrow R, allows the operator to slide tunneling member 92 out from a channel of handle 950. According to an exemplary embodiment, which is illustrated in an enlarged detail included in FIG. 9B, the attachment feature of handle 950 further includes a block 955 mounted within handle 950 and coupled to lever 952 via a dowel 956, wherein block 955 defines a portion 905 of the channel through which tunneling member 92 extends. Channel portion 905, when offset from, or misaligned with, a remainder of the channel, locks tunneling member 92 to handle 950, but, when lever 952 is rotated per arrow R, block 955 is moved to align channel portion 905 and thereby release tunneling member 92 from handle 950. Lever 952 may be formed from polycarbonate, and block 955 from stainless steel, PEI Ultem™ or PEEK.

It should be noted that a kit, according to some alternate embodiments, includes a plurality of handles having the above-described attachment feature for tunneling member 92 but not having the above described adjustment mechanism 97. Rather, each of the handles in the kit has a yoke, similar to yoke 951, for example, to which first end 911 of guide member 91 is attached, of a different size. Thus distance d9 is varied according to the size of the yoke of the handle selected from the kit for attachment to tunneling member 92.

Figure 10A:
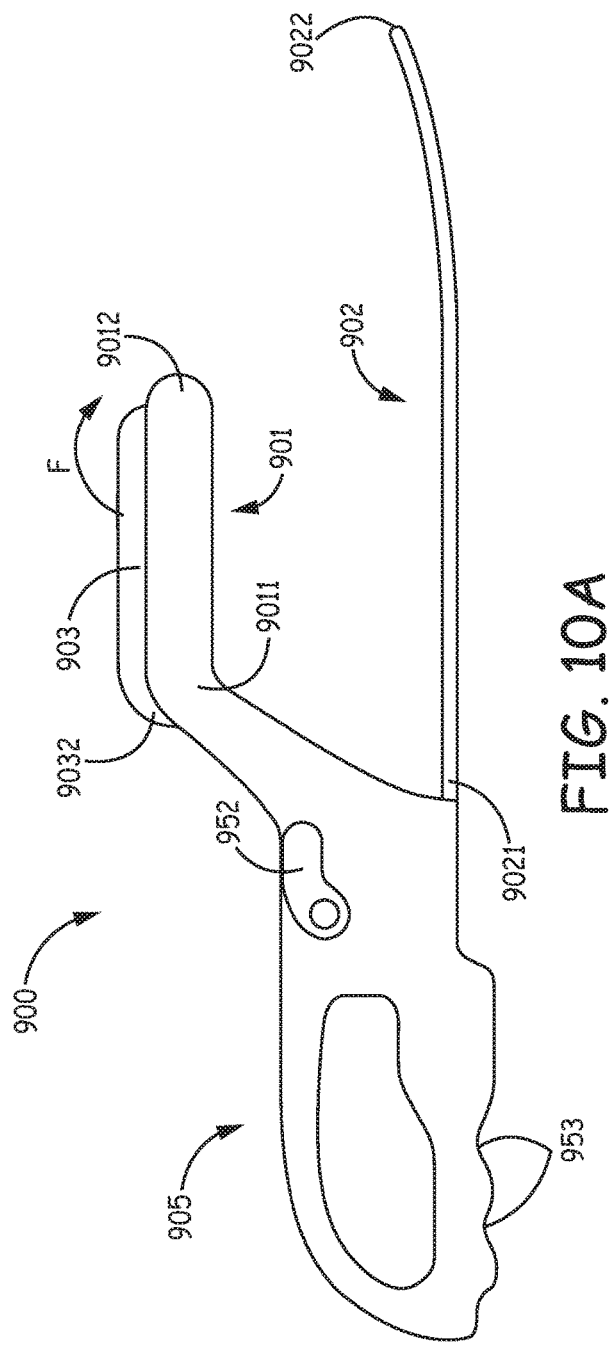
FIGS. 10A-B are plan views of another type of tool, according to some embodiments.
Figure 10B:
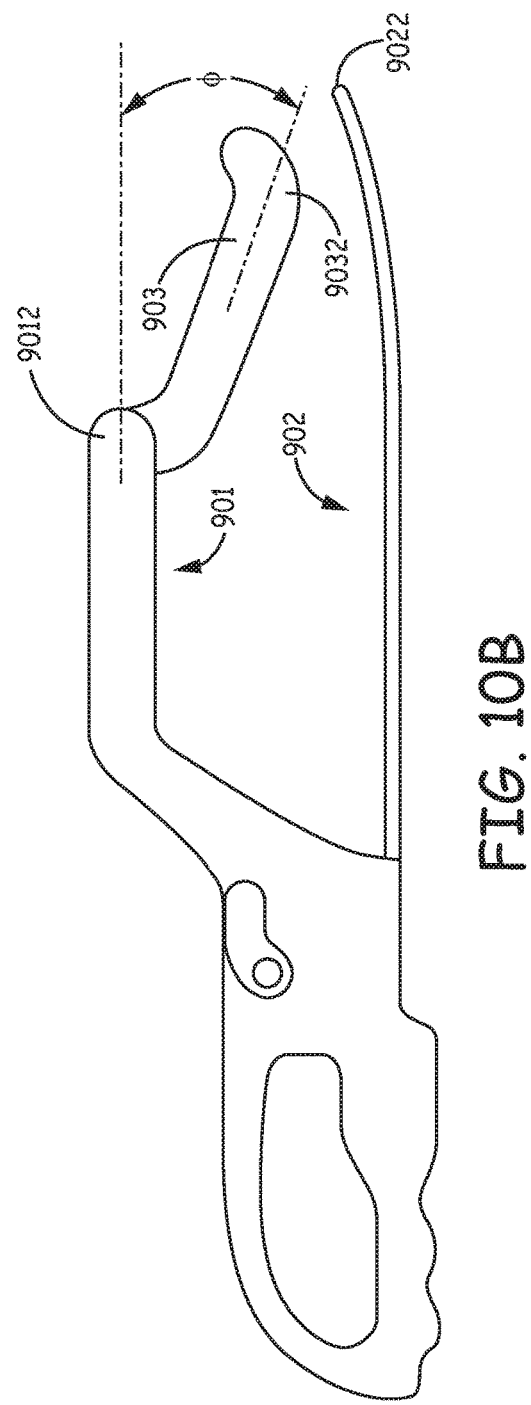

FIGS. 10A-B are plan views of another type of tool 900, according to some embodiments. FIGS. 10A-B illustrate tool 900 including a relatively straight guide member 901 and a tunneling member 902 that extend alongside and coplanar with one another, wherein guide member 901 extends from a first end 9011 thereof to a second end 9012 thereof, and tunneling member 902 extends from a first end 9021 thereof to a blunt tip 9022 thereof, both in the same direction. Tool 900 is also shown including a handle 905 coupled to first ends 9011, 9021 of guide and tunneling members 901, 902, and including a looped gripping portion with finger recesses 953 formed therein, like handle 95 of tool 90. Handle 905 of tool 900 may include the attachment feature described above for tool 90, which is configured to reversibly secure handle 905 to first end 9021 of tunneling member 902, and includes lever 952 operable to alternately release and secure tunneling member first end 9021.

FIGS. 10A-B further illustrate tool 900 including an extension tip 903 joined to second end 9012 of guide member 901 by a pivot joint, wherein extension tip 903 is moveable, per arrow F, from a retracted position (FIG. 10A) alongside guide member 901 and between the first and second ends 9011, 9012 thereof, to an extended position (FIG. 10B) extending away from guide member second end 9012 and toward blunt tip 9022 of tunneling member 902. With reference back to FIG. 6D, if the operator initially orients tool 900 in a similar fashion to that illustrated for tool 50, while inserting blunt tip 9022 of tunneling member 902 through incision site IS, the operator will likely have extension tip 903 in the retracted position until gaining sub-sternal access. Then, with reference to FIG. 10C, after gaining sub-sternal access, the operator may move tip 903 to the extended position at which a free end 9032 of tip 903 'rides' adjacent to the patient's epidermis as the operator advances tunneling member 902 in the superior direction, per arrow SUP, to create a sub-sternal tunnel. According to some embodiments, extension tip 903, once moved toward the extended position, is free to move under its own weight toward tunneling member 902, thus, with reference back to FIG. 10B, an angle φ at which the extended extension tip 903 extends relative to guide member 901 is free to change according to the size of the patient. According to the illustrated embodiment, at the extended position, free end 9032 of extension tip 903 approximately indicates a location of the underlying blunt tip 922 of tunneling member 92, as a reference for the operator.

In the foregoing detailed description, various tool features have been described with reference to specific embodiments. However, it may be appreciated that various modifications and changes can be made without departing from the scope of the invention as set forth in the appended claims. For example, one or more features of a particular exemplary embodiment may be employed by other exemplary embodiments in the same or alternative forms. Additionally, any of the various tools may be packaged with a lead, such as the exemplary lead 16 of FIG. 1A, to form a kit.

The invention claimed is:

1. A tool for creating a sub-sternal tunnel in a patient, the tool comprising:
a relatively straight guide member extending from a first end thereof to a second end thereof;
a tunneling member extending from a first end thereof to a blunt tip thereof, the blunt tip configured for blunt dissection, the tunneling member comprising an elongate rod unitary with the first end and the blunt tip, the tunneling member extending alongside and coplanar with the guide member, the first end of the tunneling member and the first end of the guide member being joined together; and
a handle coupled to the guide member, wherein the handle includes an adjustment mechanism configured to allow adjustment of a distance between the first end of the guide member and the first end of the tunneling member, the distance being coplanar with the tunneling member and the guide member, and wherein the adjustment mechanism is configured to maintain the distance during application of a force to the handle to tunnel the tunneling member through tissue,
wherein the guide member comprises a first section, a second section, and a hinge member joining the first section to the second section, the first section extending from the first end of the guide member to the hinge member, and the second section extending from the hinge member to the second end of the guide member.

2. The tool of claim 1, wherein one or both of the tunneling member and the guide member has an elastic property that spring biases the tip of the tunneling member and the second end of the guide member toward one another.

3. The tool of claim 1, wherein the tunneling member has a pre-formed curvature that biases the tip toward the guide member.

4. The tool of claim 3, wherein the tunneling member includes a first section that extends approximately parallel to the guide member, and a second section that has the pre-formed curvature.

5. The tool of claim 1, wherein the handle is coupled to the first end of the guide member and to the first end of the tunneling member.

6. The tool of claim 5, wherein the adjustment mechanism is configured to allow a plurality of positions of the tunneling member relative to the guide member.

7. The tool of claim 5, wherein the adjustment mechanism is configured to allow a plurality of positions of the guide member relative to the tunneling member.

8. The tool of claim 1, wherein the guide member and handle comprise opposing parts configured to snap fit around the first end of the tunneling member.

9. The tool of claim 1, wherein the handle includes a looped gripping portion.

10. The tool of claim 1, wherein the handle extends at an angle with respect to the relatively straight extent of the guide member, the angle being coplanar with the guide member and the tunneling member.

11. The tool of claim 10, wherein the handle includes a first finger recess and a second finger recess, the first finger recess being located in proximity to the first end of the guide member, and the second finger recess being located in proximity to the first end of the tunneling member.

12. The tool of claim 11, wherein the adjustment mechanism is located in proximity to the first and second finger recesses.

13. The tool of claim 10, wherein the handle has a bulbous contour.

14. The tool of claim 13, wherein the first end of the tunneling member is coupled to the handle via a threaded interface, and the handle is rotatable relative to the guide member to adjust, via the threaded interface, a distance between the guide member and the tunneling member, the distance being in proximity to the first ends of each.

15. The tool of claim 1, wherein the guide member includes a bubble level indicator mounted thereon.

16. The tool of claim 1, wherein the handle is a unitary handle.

17. The tool of claim 1 wherein the elongate rod is a continuous rod comprising the first end and the blunt tip, and wherein the continuous rod extends from the first end to an end of the blunt tip.

18. A tool for creating a sub-sternal tunnel in a patient, the tool comprising:
a relatively straight guide member extending from a first end thereof to a second end thereof;
a tunneling member extending from a first end thereof to a blunt tip thereof, the blunt tip configured for blunt dissection, the tunneling member comprising an elongate rod unitary with the first end and the blunt tip, the tunneling member extending alongside and coplanar with the guide member, the first end of the tunneling member and the first end of the guide member being joined together; and
a handle coupled to the guide member, wherein the handle includes an adjustment mechanism configured to allow adjustment of a distance between the first end of the guide member and the first end of the tunneling member, the distance being coplanar with the tunneling member and the guide member, and wherein the adjustment mechanism is configured to maintain the distance during application of a force to the handle to tunnel the tunneling member through tissue,
wherein the guide member and the handle are integrally formed from a relatively rigid medical grade plastic material.

19. A tool for creating a sub-sternal tunnel in a patient, the tool comprising:
a relatively straight guide member extending from a first end thereof to a second end thereof;
a tunneling member extending from a first end thereof to a blunt tip thereof, the blunt tip configured for blunt dissection, the tunneling member comprising an elongate rod unitary with the first end and the blunt tip, the tunneling member extending alongside and coplanar with the guide member, the first end of the tunneling member and the first end of the guide member being joined together;
a handle coupled to the guide member, wherein the handle includes an adjustment mechanism configured to allow adjustment of a distance between the first end of the guide member and the first end of the tunneling member, the distance being coplanar with the tunneling member and the guide member, and wherein the adjustment mechanism is configured to maintain the distance during application of a force to the handle to tunnel the tunneling member through tissue; and
an extension tip joined to the second end of the guide member, the extension tip being moveable from a first position to a second position;
wherein, at the first position, the extension tip extends alongside the guide member between the first and second ends thereof; and
at the second position, the extension tip extends away from the second end of the guide member.

20. The tool of claim 19, wherein, at the second position, the extension tip also extends toward the tunneling member.

21. A handle for a tunneling tool, the handle comprising:
a guide member extending from a first end to a second end;
an attachment feature configured to reversibly secure the handle to a first end of a tunneling member so that the secured tunneling member extends alongside and coplanar with the guide member, wherein when the attachment feature reversibly secures the handle to the first end of the tunneling member, the handle surrounds the first end of the tunneling member;
a gripping portion located in proximity to the attachment feature and the first end of the guide member; and
an adjustment mechanism configured to allow adjustment of a distance between the first end of the guide member and the first end of the secured tunneling member, the distance being coplanar with the tunneling member and the guide member, wherein the adjustment mechanism is configured to maintain the distance during application of a force to the handle to tunnel the tunneling member through tissue,
wherein the guide member and at least a portion of the handle are integrally formed from a relatively rigid medical grade plastic material.

22. The handle of claim 21, wherein the adjustment mechanism is configured to allow a plurality of positions of the guide member relative to the secured tunneling member.

23. The handle of claim 21, wherein the attachment feature comprises the adjustment mechanism, and wherein the attachment feature is adjustable to vary the distance between the secured first end of the tunneling member and the first end of the guide member.

24. The handle of claim 21, further comprising:
an extension tip joined to the second end of the guide member, the extension tip being moveable from a first position to a second position; and
wherein, at the first position, the extension tip extends alongside the guide member between the first and second ends thereof; and
at the second position, the extension tip extends away from the second end of the guide member.

25. The handle of claim 24, wherein the extension tip is free to move under its own weight.

* * * * *